US009672422B2

(12) United States Patent
Hakoshima

(10) Patent No.: US 9,672,422 B2
(45) Date of Patent: Jun. 6, 2017

(54) PUPIL DETECTION DEVICE AND PUPIL DETECTION METHOD

(71) Applicant: JVC KENWOOD Corporation, Yokohama-shi (JP)

(72) Inventor: Shuji Hakoshima, Yokohama (JP)

(73) Assignee: JVC KENWOOD Corporation, Yokohama-shi (JP)

( * ) Notice: Subject to any disclaimer, the term of this patent is extended or adjusted under 35 U.S.C. 154(b) by 19 days.

(21) Appl. No.: 14/806,350

(22) Filed: Jul. 22, 2015

(65) Prior Publication Data

US 2016/0026863 A1 Jan. 28, 2016

(30) Foreign Application Priority Data

Jul. 23, 2014 (JP) ................................ 2014-150138
Nov. 7, 2014 (JP) ................................ 2014-227056

(51) Int. Cl.
*G06K 9/00* (2006.01)
*G06K 9/78* (2006.01)
(Continued)

(52) U.S. Cl.
CPC ........ *G06K 9/00604* (2013.01); *A61B 3/0025* (2013.01); *A61B 3/113* (2013.01);
(Continued)

(58) Field of Classification Search
CPC ... G06T 7/0085; G06T 7/0042; G06T 7/0022; G06T 7/0075; G06T 7/602; G06T 2207/30201; G06T 2207/10028; G06T 2207/10012; G06T 7/60; G06T 7/606; G06T 2207/30041; G06K 9/78; G06K 9/0061; G06K 9/00604; H04N 13/0239;
(Continued)

(56) References Cited

U.S. PATENT DOCUMENTS

2004/0252865 A1* 12/2004 Tisse .................. G06K 9/00268
382/117
2006/0147094 A1* 7/2006 Yoo .................... G06K 9/00604
382/117

(Continued)

FOREIGN PATENT DOCUMENTS

| JP | 2002-000567 A | 1/2002 |
|---|---|---|
| JP | 2004-062393 A | 2/2004 |
| JP | 2012-024154 A | 2/2012 |

OTHER PUBLICATIONS

English translation of Japanese Patent Publication JP2002-567.*
Extended European Search Report in European Patent Application No. 15177685.3, dated Dec. 16, 2015.

Primary Examiner — Jon Chang
(74) *Attorney, Agent, or Firm* — Venable LLP; Michael A. Sartori; F. Brock Riggs

(57) ABSTRACT

A pupil detection device includes an identification unit that identifies a pupil region from a captured image of an eye, an extractor that extracts a contour of the pupil region identified by the identification unit, a selector that selects a plurality of points on the contour of the pupil region extracted by the extractor, a center calculator that calculates a center of a circle passing through the plurality of points selected by the selector, and a pupil detector that detects a center of the pupil region from the center of a circle calculated by the center calculator.

6 Claims, 32 Drawing Sheets

(51) Int. Cl.
  *G06T 7/00*    (2006.01)
  *G06T 7/60*    (2006.01)
  *A61B 3/00*    (2006.01)
  *A61B 3/113*   (2006.01)
  *H04N 13/02*   (2006.01)
  *A61B 3/107*   (2006.01)
  *A61B 3/11*    (2006.01)

(52) U.S. Cl.
  CPC ............ *G06K 9/0061* (2013.01); *G06K 9/78* (2013.01); *H04N 13/0239* (2013.01); *H04N 13/0253* (2013.01); *A61B 3/107* (2013.01); *A61B 3/112* (2013.01); *G06T 2207/10012* (2013.01); *G06T 2207/10028* (2013.01); *G06T 2207/30201* (2013.01)

(58) Field of Classification Search
  CPC ... H04N 13/0253; A61B 3/0025; A61B 3/113; A61B 3/107; A61B 3/112
  USPC .................................. 382/103, 117; 351/200
  See application file for complete search history.

(56) References Cited

U.S. PATENT DOCUMENTS

| | | | |
|---|---|---|---|
| 2008/0069410 A1* | 3/2008 | Ko | G06K 9/0061 382/117 |
| 2008/0253622 A1* | 10/2008 | Tosa | G06K 9/00604 382/117 |
| 2009/0220126 A1* | 9/2009 | Claret-Tournier | G06K 9/0061 382/117 |
| 2011/0267447 A1 | 11/2011 | Su et al. | |

\* cited by examiner

FIG.22

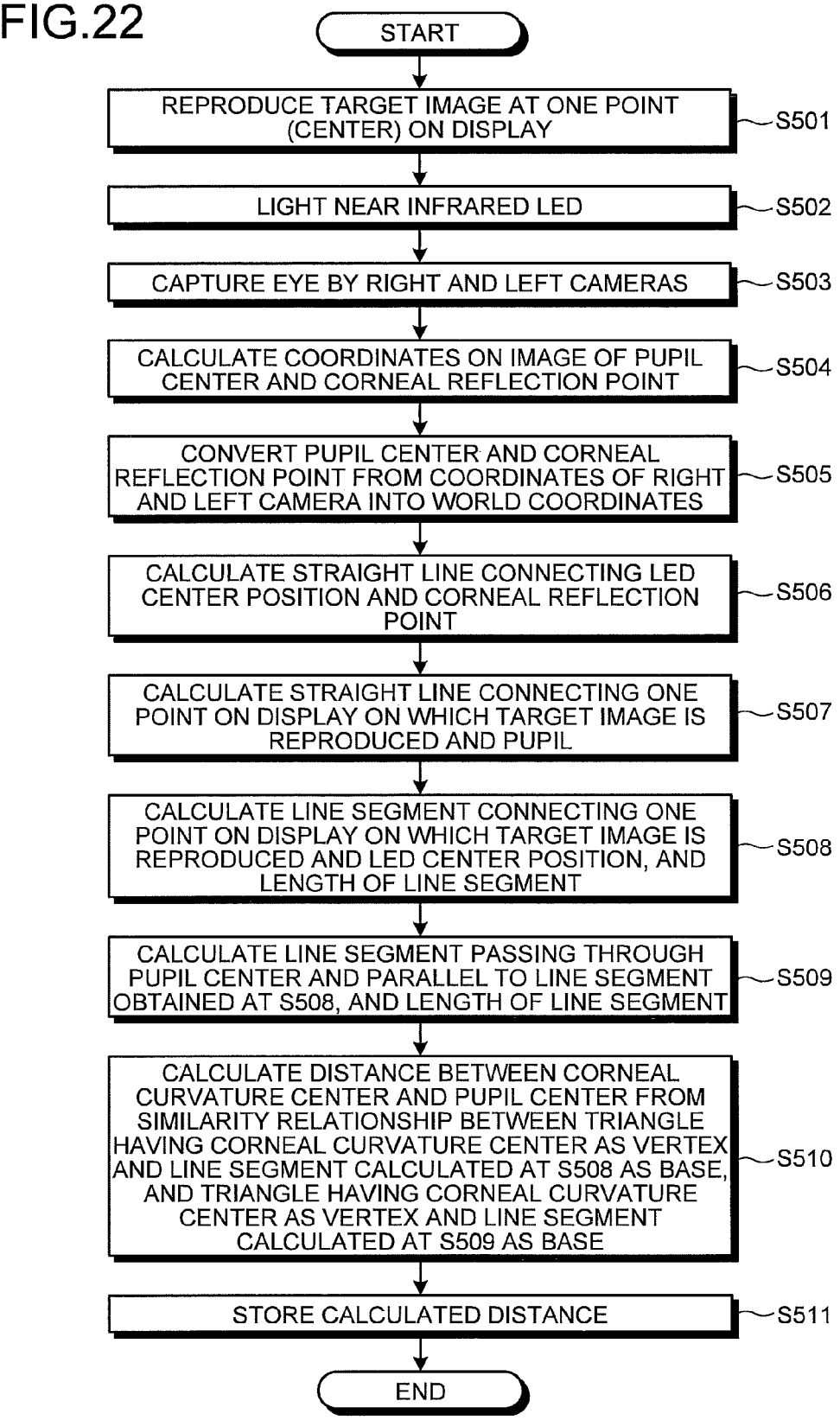

START
↓
S501 — REPRODUCE TARGET IMAGE AT ONE POINT (CENTER) ON DISPLAY
↓
S502 — LIGHT NEAR INFRARED LED
↓
S503 — CAPTURE EYE BY RIGHT AND LEFT CAMERAS
↓
S504 — CALCULATE COORDINATES ON IMAGE OF PUPIL CENTER AND CORNEAL REFLECTION POINT
↓
S505 — CONVERT PUPIL CENTER AND CORNEAL REFLECTION POINT FROM COORDINATES OF RIGHT AND LEFT CAMERA INTO WORLD COORDINATES
↓
S506 — CALCULATE STRAIGHT LINE CONNECTING LED CENTER POSITION AND CORNEAL REFLECTION POINT
↓
S507 — CALCULATE STRAIGHT LINE CONNECTING ONE POINT ON DISPLAY ON WHICH TARGET IMAGE IS REPRODUCED AND PUPIL
↓
S508 — CALCULATE LINE SEGMENT CONNECTING ONE POINT ON DISPLAY ON WHICH TARGET IMAGE IS REPRODUCED AND LED CENTER POSITION, AND LENGTH OF LINE SEGMENT
↓
S509 — CALCULATE LINE SEGMENT PASSING THROUGH PUPIL CENTER AND PARALLEL TO LINE SEGMENT OBTAINED AT S508, AND LENGTH OF LINE SEGMENT
↓
S510 — CALCULATE DISTANCE BETWEEN CORNEAL CURVATURE CENTER AND PUPIL CENTER FROM SIMILARITY RELATIONSHIP BETWEEN TRIANGLE HAVING CORNEAL CURVATURE CENTER AS VERTEX AND LINE SEGMENT CALCULATED AT S508 AS BASE, AND TRIANGLE HAVING CORNEAL CURVATURE CENTER AS VERTEX AND LINE SEGMENT CALCULATED AT S509 AS BASE
↓
S511 — STORE CALCULATED DISTANCE
↓
END

PUPIL DETECTION DEVICE AND PUPIL DETECTION METHOD

CROSS-REFERENCE TO RELATED APPLICATION(S)

The present application claims priority to and incorporates by reference the entire contents of Japanese Patent Application No. 2014-150138 filed in Japan on Jul. 23, 2014 and Japanese Patent Application No. 2014-227056 filed in Japan on Nov. 7, 2014.

BACKGROUND OF THE INVENTION

1. Field of the Invention

The present invention relates to a pupil detection technology.

2. Description of the Related Art

With the advance of an increase in precision and processing speed, and downsizing of cameras, visual line detection devices that detect a position on an observation surface such as a monitor screen that a subject is gazing at, from an image of a face captured by a camera have been proposed. Initially, many of technologies require fixation of the head of the subject, and attaching of a detection device to the head. Recently, to decrease a burden of the subject, non-contact type visual line detection devices without requiring attaching of a device to the head have been developed, and visual line detection devices with higher precision are demanded. The non-contact type visual line detection devices detect a visual line according to a positional relationship between a pupil and corneal reflection on an image of the camera. Therefore, it is important to accurately obtain pupil center coordinates and corneal reflection center coordinates on the image of the camera.

Japanese Laid-open Patent Publication No. 2012-024154 proposes a technology that can stably detect a pupil using information of a corneal reflection image in a positive manner even if a most part of the pupil is hidden by the corneal reflection.

A contour of the pupil is originally a circular shape, but there is a case where the pupil is blocked by the corneal reflection, and a part of the pupil is lacked. Even for such an image in which the part of the pupil is lacked, it is desirable to detect a pupil center in a high accurate manner.

SUMMARY OF THE INVENTION

It is an object of the present invention to at least partially solve the problems in the conventional technology.

There is provided a pupil detection device that includes an identification unit that identifies a pupil region from a captured image of an eye, an extractor that extracts a contour of the pupil region identified by the identification unit, a selector that selects a plurality of points on the contour of the pupil region extracted by the extractor, a center calculator that calculates a center of a circle passing through the plurality of points selected by the selector, and a pupil detector that detects a center of the pupil region from the center of a circle calculated by the center calculator.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 22 is a flowchart illustrating an example of the calculation processing of the second modification;

DETAILED DESCRIPTION OF THE PREFERRED EMBODIMENTS

Hereinafter, embodiments of a pupil detection device and a pupil detection method according to the present invention will be described in detail based on the drawings. Note that the invention is not limited by the embodiments. Further, hereinafter, an example of using the pupil detection device as a diagnosis supporting device will be described. The diagnosis supporting device supports diagnosis of developmental disorder, using a detection result of a visual line. An applicable device is not limited to the diagnosis supporting device.

A pupil detection device (diagnosis supporting device) of the present embodiment detects a visual line, using an illuminator installed in one place. Further, the pupil detection device (diagnosis supporting device) of the present embodiment calculates a corneal curvature center position in a high accurate manner, using a result of measurement obtained by causing a subject to gaze at one point, before detection of the visual line.

Note that the illuminator is an element that includes a light source and can irradiate an eye ball of the subject with light. The light source is an element that emits light, such as a light emitting diode (LED). The light source may be configured from one LED, or may be configured such that a plurality of LEDs is combined and is arranged at one place. Hereinafter, "light source" may be used as a term that indicates the illuminator.

Figure 1:
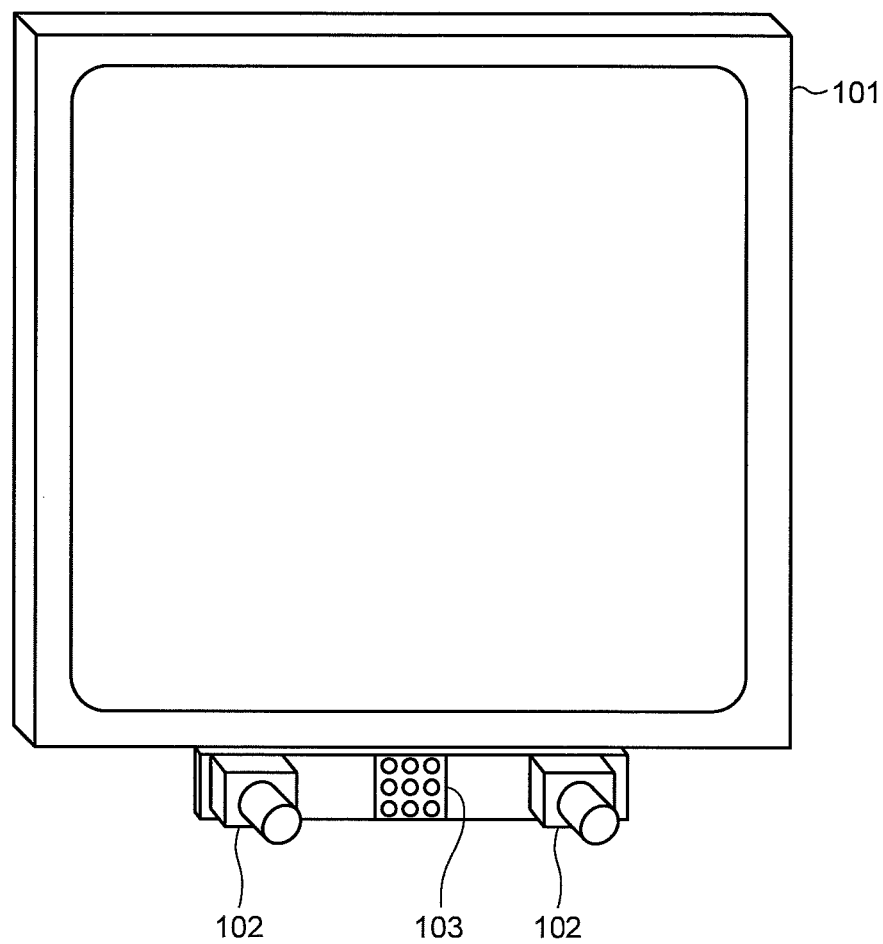
FIG. 1 is a diagram illustrating an example of arrangement of a display, a stereo camera, an infrared light source of the present embodiment.
Figure 2:
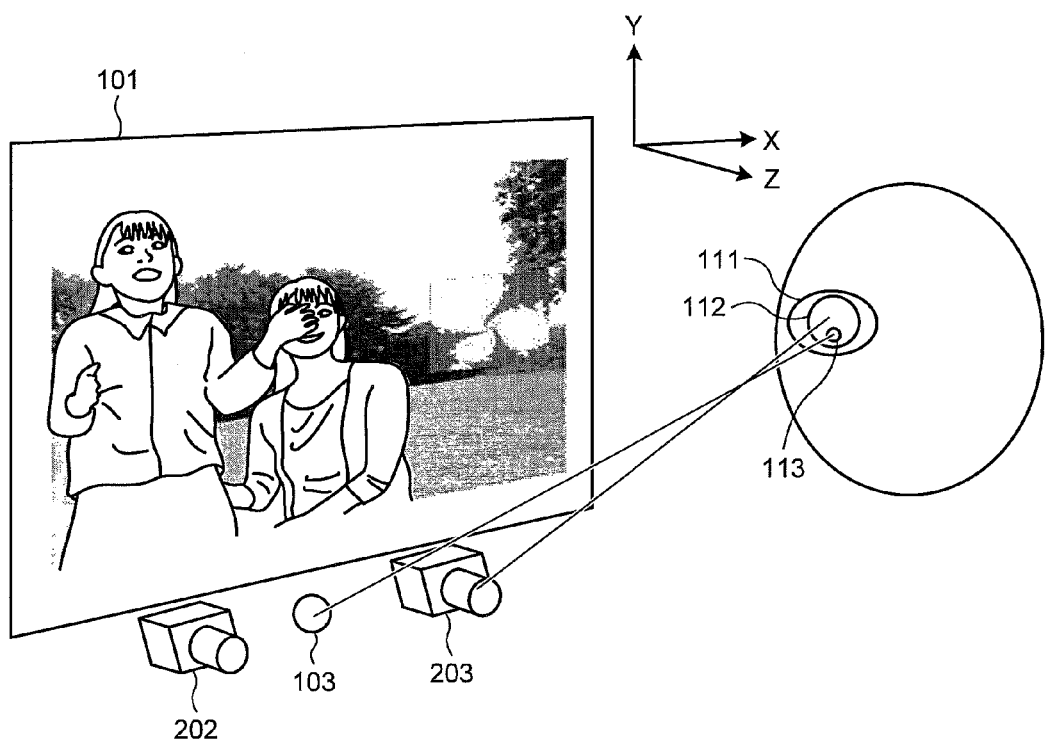
FIG. 2 is a diagram illustrating an example of arrangement of the display, the stereo camera, the infrared light source of the present embodiment, and a subject.

FIGS. 1 and 2 are diagrams illustrating an example of arrangement of a display, a stereo camera, an infrared light source of the present embodiment and a subject.

As illustrated in FIG. 1, a diagnosis supporting device of the present embodiment includes a display 101, a stereo camera 102, and an LED light source 103. The stereo camera 102 is arranged under the display 101. The LED light source 103 is arranged at a center position of two cameras included in the stereo camera 102. The LED light source 103 is, for example, a light source that irradiates the subject with a near infrared ray with a wavelength of 850 nm. FIG. 1 illustrates an example in which the LED light source 103 (illuminator) is configured from nine LEDs. Note that, in the stereo camera 102, a lens that can transmit near infrared light with a wavelength of 850 nm is used.

As illustrated in FIG. 2, the stereo camera 102 includes a right camera 202 and a left camera 203. The LED light source 103 irradiates an eye ball 111 of the subject with the near infrared light. In an image obtained by the stereo camera 102, a pupil 112 is reflected at low luminance and becomes dark, and corneal reflection 113 caused in the eye ball 111, as a virtual image, is reflected at high luminance and becomes bright. Therefore, positions of the pupil 112 and the corneal reflection 113 on the image can be obtained by the two cameras (the right camera 202 and the left camera 203).

Further, three-dimensional world coordinate values of positions of the pupil 112 and the corneal reflection 113 are calculated from the positions of the pupil 112 and the corneal reflection 113 obtained by the two cameras. In the present embodiment, as the three-dimensional world coordinates, a coordinate in an up and down direction is a Y coordinate (the up direction is +), a coordinate in a transverse direction is an X coordinate (the right direction is +), and a coordinate in a depth direction is a Z coordinate (the front side is +), where a middle position on the screen of the display 101 is the origin.

Figure 3:
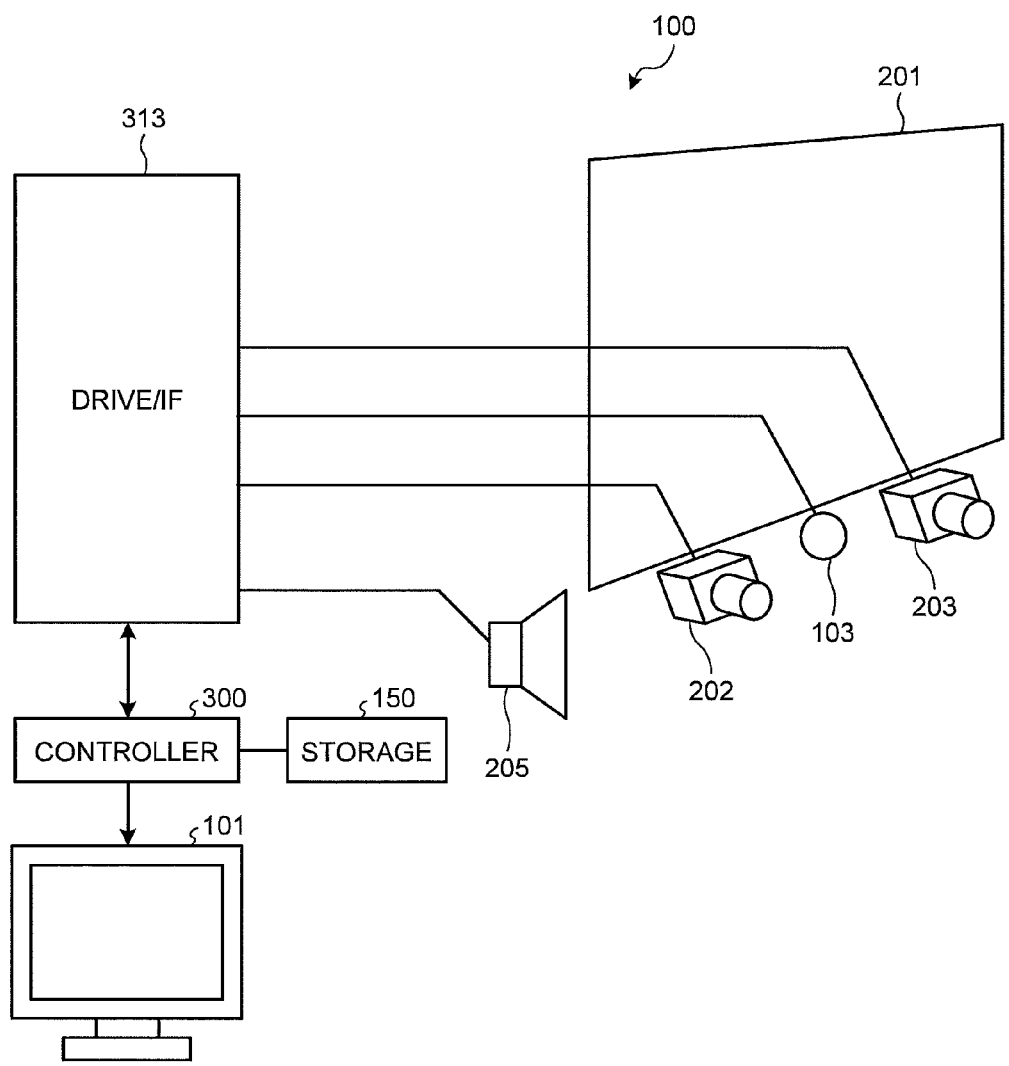
FIG. 3 is a diagram illustrating an outline of functions of a diagnosis supporting device.

FIG. 3 is a diagram illustrating an outline of functions of the diagnosis supporting device 100. FIG. 3 illustrates a part of the configurations illustrated in FIGS. 1 and 2, and configurations used for driving the aforementioned configurations. As illustrated in FIG. 3, the diagnosis supporting device 100 includes the right camera 202, the left camera 203, the LED light source 103, a speaker 205, a drive/IF (interface) 313, a controller 300, a storage 150, and the display 101. In FIG. 3, a positional relationship between a display screen 201, and the right camera 202 and the left camera 203 is illustrated in an easily understandable manner. The display screen 201 is a screen displayed in the display 101. Note that the driver and the IF may be integrated or separated.

The speaker 205 functions as an audio output unit that outputs an audio and the like for prompting the subject to pay attention, at the time of calibration and the like.

The drive/IF 313 drives units included in the stereo camera 102. Further, the drive/IF 313 serves as an interface between the units included in the stereo camera 102, and the controller 300.

The controller 300 can be realized by a computer that includes a control device such as a central processing unit (CPU), a storage device such as read only memory (ROM) and random access memory (RAM), a communication I/F that is connected with a network and performs communication, and a bus that connects the units.

The storage 150 stores various types of information such as a control program, a measurement result, and a diagnosis support result. The storage 150 stores an image to be displayed in the display 101, and the like. The display 101 displays various types of information such as an object image for diagnosis, and the like.

Figure 4:
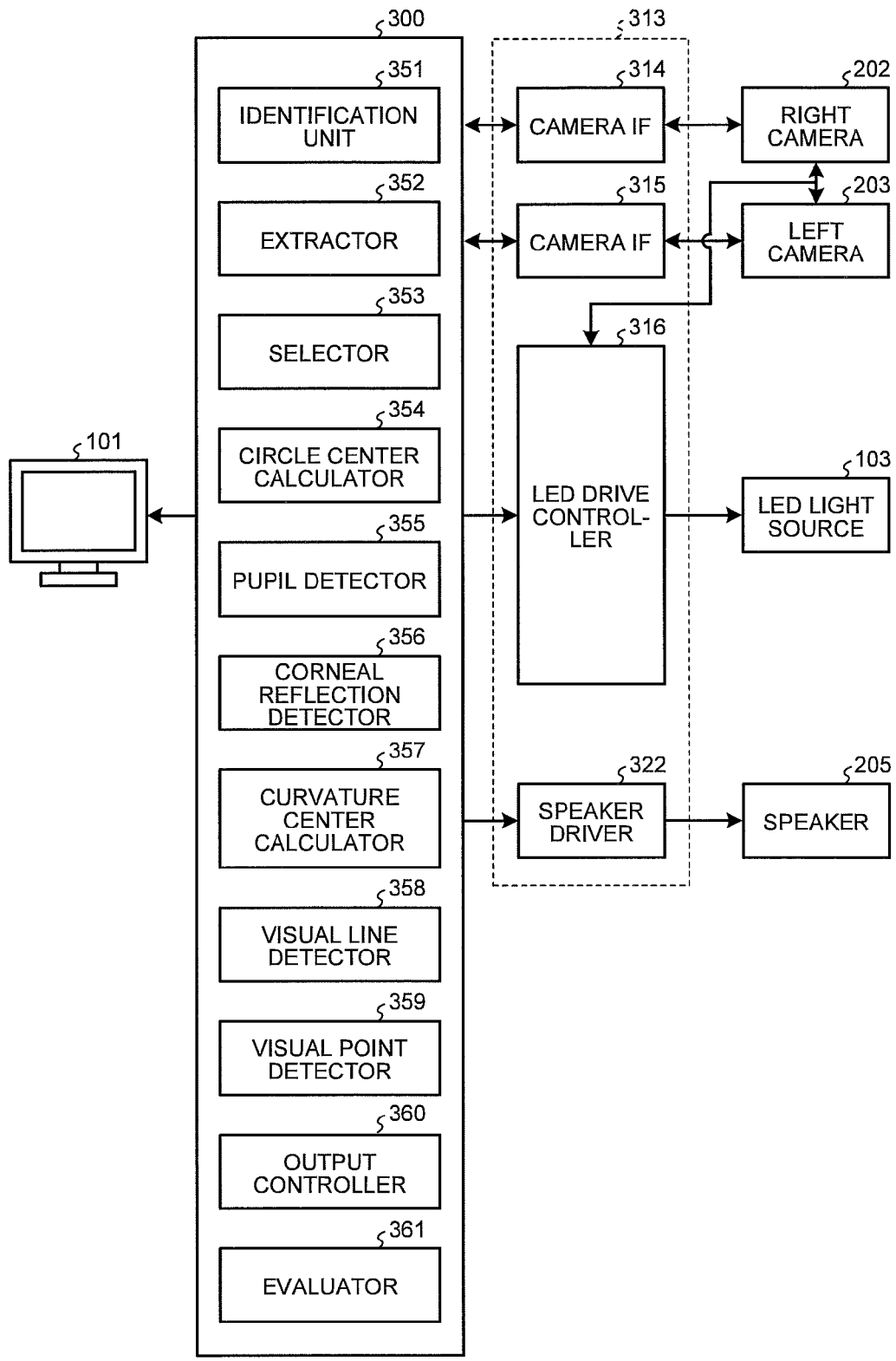
FIG. 4 is a block diagram illustrating an example of detailed functions of respective units illustrated in FIG. 3.

FIG. 4 is a block diagram illustrating an example of detailed functions of the respective units illustrated in FIG. 3. As illustrated in FIG. 4, the display 101 and the drive/IF 313 are connected to the controller 300. The drive/IF 313 includes camera IFs 314 and 315, an LED drive controller 316, and a speaker driver 322.

The right camera 202 and the left camera 203 are connected to the drive/IF 313 through the camera IFs 314 and 315, respectively. The drive/IF 313 drives these cameras to capture the subject.

The speaker driver 322 drives the speaker 205. Note that the diagnosis supporting device 100 may include an interface (printer IF) for being connected with a printer as a print unit. Further, the printer may be included inside the diagnosis supporting device 100.

The controller 300 controls the entire diagnosis supporting device 100. The controller 300 includes an identification unit 351, an extractor 352, a selector 353, a circle center calculator 354, a pupil detector 355, a corneal reflection detector 356, a curvature center calculator 357, a visual line detector 358, a visual point detector 359, an output controller 360, and an evaluator 361. Note that, as the pupil detection device, the controller 300 may just include at least the identification unit 351, the extractor 352, the selector 353, the circle center calculator 354, and the pupil detector 355.

The elements (the identification unit 351, the extractor 352, the selector 353, the circle center calculator 354, the pupil detector 355, the corneal reflection detector 356, the curvature center calculator 357, the visual line detector 358, the visual point detector 359, the output controller 360, and the evaluator 361) included in the controller 300 may be realized by software (programs), may be realized by a hardware circuit, or may be realized by use of the software and the hardware circuit together.

When the elements are realized by the programs, the programs are recorded in a computer-readable recording medium such as a compact disk read only memory (CD-ROM), a flexible disk (FD), a compact disk recordable (CD-R), or a digital versatile disk (DVD) in a file in an installable format or in an executable format, and provided as a computer program product. The programs may be stored on a computer connected to a network such as the Internet, and provided by being downloaded through the network. Further, the programs may be provided or distributed through the network such as the Internet. Further, the programs may be provided by being incorporated in ROM or the like in advance.

The identification unit 351 identifies a pupil region from an image of an eye ball captured by the stereo camera 102. The extractor 352 extracts a contour of the pupil region identified by the identification unit 351. The selector 353 selects a plurality of points on the contour of the pupil region, the contour being extracted by the extractor 352. The circle center calculator 354 calculates a center of a circle that passes through the plurality of points selected by the selector 353. The pupil detector 355 detects a center of the pupil region based on the center of the circle calculated by the circle center calculator 354. That is, the pupil detector 355 detects a position (first position) of a pupil center that indicates the center of the pupil. The corneal reflection detector 356 calculates a position (second position) of a corneal reflection center that indicates the center of corneal reflection, from the captured image of the eye ball. The pupil detector 355 and the corneal reflection detector 356 correspond to a position detector that detects the first position that indicates the center of the pupil, and the second position that indicates the center of the corneal reflection.

The curvature center calculator 357 calculates a corneal curvature center (fourth position) from a straight line (first straight line) that connects the LED light source 103 and the corneal reflection center. For example, the curvature center calculator 357 calculates a position where the distance from the corneal reflection center becomes a predetermined value, on the straight line, as the corneal curvature center. As the predetermined value, a value determined from a curvature radius value of a typical cornea in advance, or the like can be used.

The curvature radius value of a cornea varies among different individuals, and thus an error may become large if the corneal curvature center is calculated using the value determined in advance. Therefore, the curvature center calculator 357 may calculate the corneal curvature center in consideration of the individual difference. In this case, first, the curvature center calculator 357 calculates an intersection point of a straight line (second straight line) that connects the pupil center and a target position, and the straight line (first straight line) that connects the corneal reflection center and the LED light source 103, using the pupil center and the corneal reflection center calculated when the subject is caused to gaze at the target position (third position). The curvature center calculator 357 then calculates a distance (first distance) between the pupil center and the calculated intersection point, and stores the calculated distance in the storage 150, for example.

The target position may be any position as long as the position can be determined in advance, and three-dimensional world coordinate values can be calculated. For example, a middle position (the origin of the three-dimensional world coordinates) of the display screen 201 can be used as the target position. In this case, for example, the output controller 360 displays an image (target image) or the like that the subject is caused to gaze at, in the target position (center) on the display screen 201. Accordingly, the subject can gaze at the target position.

The target image may be any image as long as the image can draw attention from the subject. For example, an image with a varying display form such as luminance or a color, an image having different display form from other regions, or the like can be used as the target image.

Note that the target position is not limited to the center of the display screen 201, and any position can be employed. If the center of the display screen 201 is employed as the target position, the distance between the center and any end part of the display screen 201 is minimized. Therefore, for example, a measurement error at the time of detecting the visual line can be made smaller.

Processing up to the calculation of the distance is executed in advance before actual detection of the visual line is started. At the time of actual detection of the visual line, the curvature center calculator 357 calculates a position where the distance from the pupil center becomes the distance calculated in advance, on the straight line that connects the LED light source 103 and the corneal reflection center, as the corneal curvature center. The curvature center calculator 357 corresponds to a calculator that calculates the corneal curvature center (fourth position) from the position of the LED light source 103, the predetermined position (third position) that indicates the target image on the display, the position of the pupil center, and the position of the corneal reflection center.

The visual line detector 358 detects the visual line of the subject from the pupil center and the corneal curvature center. For example, the visual line detector 358 detects a direction from the corneal curvature center toward the pupil center, as a visual line direction of the subject.

The visual point detector 359 detects a visual point of the subject, using the detected visual line direction. The visual point detector 359 detects, for example, a visual point (gazing visual point) that is a point that the subject gazes at on the display screen 201. The visual point detector 359 detects an intersection point of a visual line vector and an XY plane, which are expressed in a three-dimensional world coordinate system as illustrated in FIG. 2, as the gazing visual point of the subject.

The output controller 360 controls output of various types of information to the display 101, the speaker 205, and the like. For example, the output controller 360 outputs the target image to the target position on the display 101. Further, the output controller 360 controls output to the display 101, such as a diagnosis image, an evaluation result by the evaluator 361, and the like.

The diagnosis image may just be an image according to evaluation processing based on a visual line (visual point) detection result. For example, when a developmental disorder is diagnosed, a diagnosis image that includes an image (a geometrical pattern picture or the like) preferred by the subject with the developmental disorder, and another image (a picture of a person, or the like) may be used.

The evaluator 361 performs evaluation processing based on the diagnosis image, and the gazing visual point detected by the visual point detector 359. For example, when the developmental disorder is diagnosed, the evaluator 361 analyzes the diagnosis image and the gazing visual point, and evaluates whether the subject with the developmental disorder has gazed at the image that the subject prefers.

Figure 5:
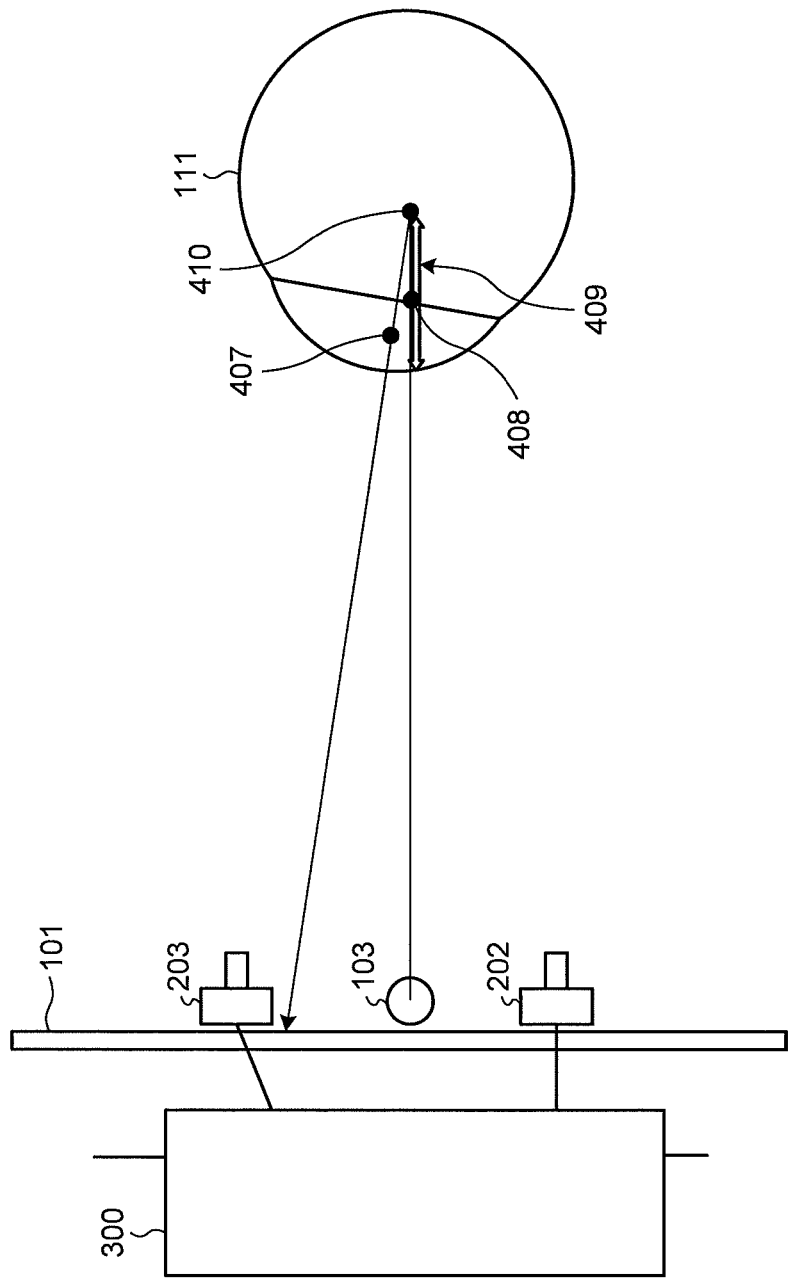
FIG. 5 is a diagram illustrating an outline of processing executed by the diagnosis supporting device of the present embodiment.

FIG. 5 is a diagram for describing an outline of processing executed by the diagnosis supporting device 100 of the present embodiment. Elements described in FIGS. 1 to 4 are denoted with the same reference signs, and description is omitted.

A pupil center 407 and a corneal reflection center 408 respectively indicate the center of the pupil and the center of a corneal reflection point detected when the LED light source 103 is lighted. A cornea curvature radius 409 indicates the distance from a surface of the cornea to a corneal curvature center 410.

Figure 6:
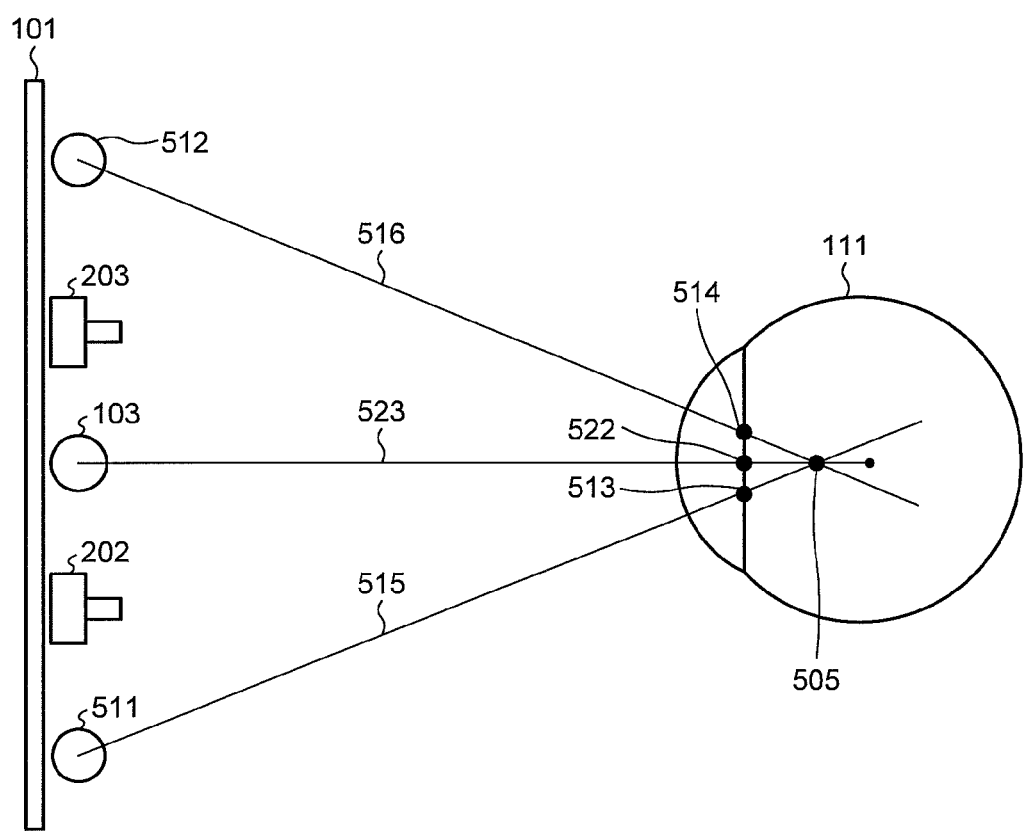
FIG. 6 is an explanatory diagram illustrating a difference between a method of using two light sources and the present embodiment using one light source.

FIG. 6 is an explanatory diagram illustrating a difference between a method using two light sources (illuminators) (hereinafter, referred to as method A), and the present embodiment using one light source (illuminator). Elements described in FIGS. 1 to 4 are denoted with the same reference signs, and description is omitted.

The method A uses two LED light sources 511 and 512, in place of the LED light source 103. In the method A, an intersection point of a straight line 515 that connects a corneal reflection center 513 and the LED light source 511 of when the LED light source 511 irradiates the subject with light, and a straight line 516 that connects a corneal reflection center 514 and the LED light source 512 of when the LED light source 512 irradiates the subject with light is calculated. This intersection point serves as a corneal curvature center 505.

In contrast, in the present embodiment, a straight line 523 that connects a corneal reflection center 522 and the LED light source 103 of when the LED light source 103 irradiates the subject with light is considered. The straight line 523 passes through the corneal curvature center 505. Further, the curvature radius of a cornea is known to have a small influence due to the individual difference and have a nearly fixed value. According to this fact, the corneal curvature center of when the LED light source 103 irradiates the subject with light exists on the straight line 523, and can be calculated using a typical curvature radius value.

However, when the visual point is calculated using the position of the corneal curvature center obtained using the typical curvature radius value, the visual point position is deviated from an original position due to the individual difference of the eye ball, and an accurate visual point position may not be able to be detected.

Figure 7:
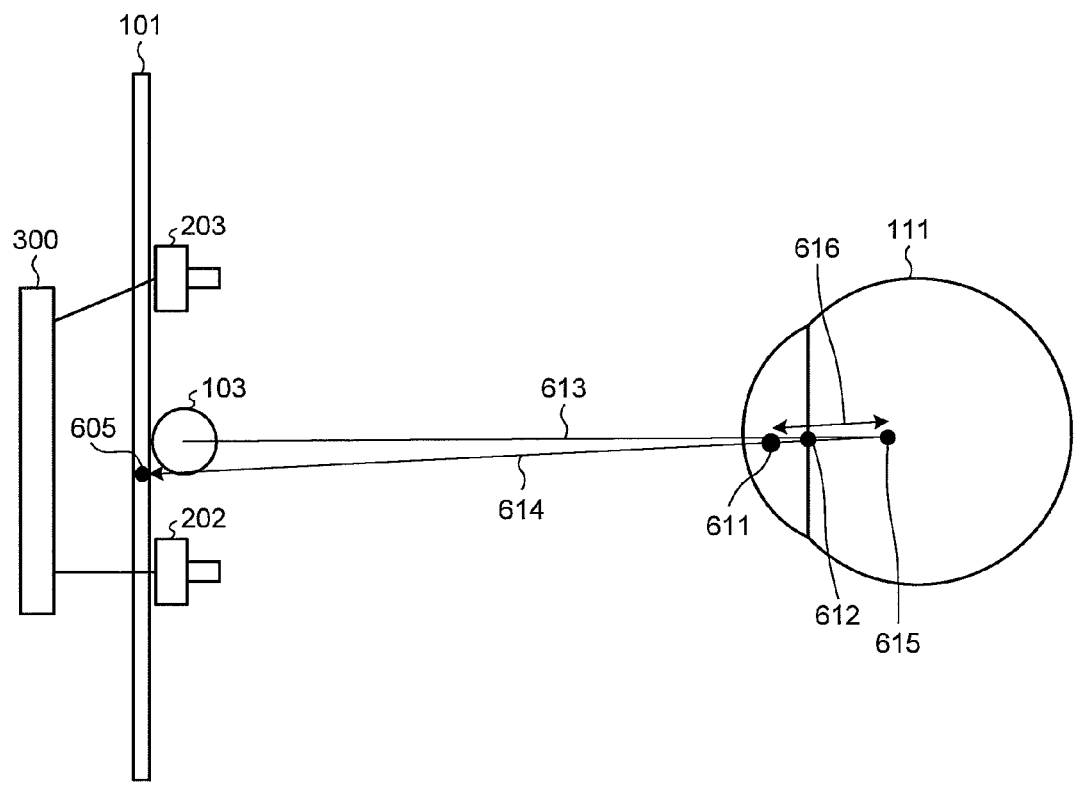
FIG. 7 is a diagram for describing calculation processing of calculating a distance between a pupil center position and a corneal curvature center position.

FIG. 7 is a diagram for describing calculation processing of calculating a corneal curvature center position, and the distance between a pupil center position and the corneal curvature center position, before the visual point detection (visual line detection) is performed. Elements described in FIGS. 1 to 4 are denoted with the same reference signs, and description is omitted. Note that connection of the right and left cameras (the right camera 202 and the left camera 203) and the controller 300 is not illustrated and is omitted.

A target position 605 is a position for causing the subject to gaze at, by outputting of a target image or the like to one point on the display 101. In the present embodiment, the target position 605 is a middle position on the screen of the display 101. A straight line 613 is a straight line that connects the LED light source 103 and a corneal reflection center 612. A straight line 614 is a straight line that connects the target position 605 (gazing visual point) that the subject gazes at and a pupil center 611. A corneal curvature center 615 is an intersection point of the straight line 613 and the straight line 614. The curvature center calculator 357 calculates and stores a distance 616 between the pupil center 611 and the corneal curvature center 615.

Figure 8:
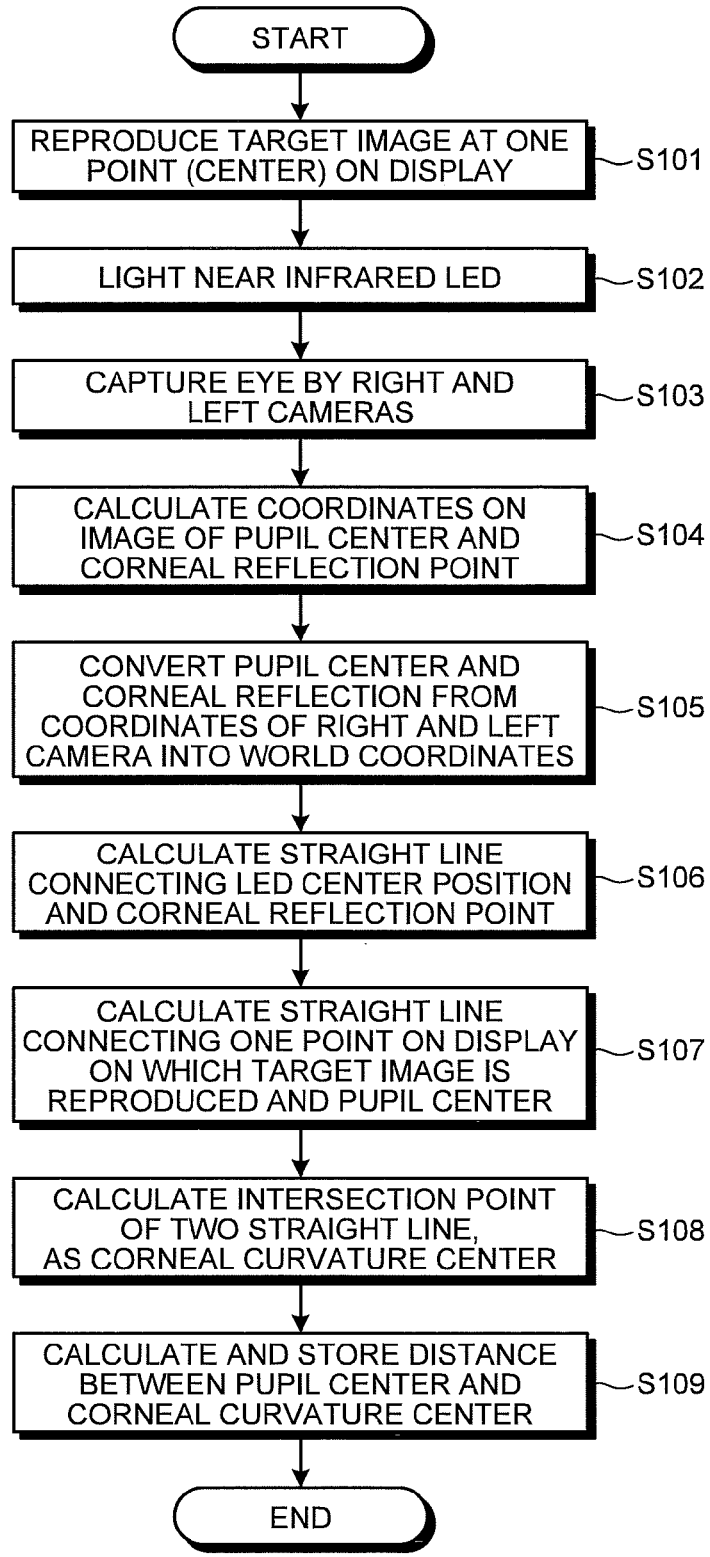
FIG. 8 is a flowchart illustrating an example of the calculation processing of the present embodiment.

FIG. 8 is a flowchart illustrating an example of calculation processing in the present embodiment.

First, the output controller 360 reproduces the target image at one point on the screen of the display 101 (step S101), and prompts the subject to gaze at the one point. Next, the controller 300 lights the LED light source 103 toward an eye of the subject, using the LED drive controller 316 (step S102). The controller 300 captures the eye of the subject by the right and left cameras (the right camera 202 and the left camera 203) (step S103).

By the irradiation of the LED light source 103, a pupil part is detected as a dark part (dark pupil). Further, as reflection of the LED irradiation, a virtual image of the corneal reflection occurs, and a corneal reflection point (corneal reflection center) is detected as a bright part. Pupil detection processing of detecting the dark pupil is executed by the identification unit 351, the extractor 352, the selector 353, the circle center calculator 354, and the pupil detector 355. The pupil detector 355, for example, calculates coordinates that indicate the position of the detected pupil center. Details of the pupil detection processing will be described below. The corneal reflection detector 356 detects a corneal reflection part from the captured image, and calculates coordinates that indicate the position of the corneal reflection center. The corneal reflection detector 356, for example, detects a region having predetermined brightness or more including a brightest part in a fixed region including the eye, as the corneal reflection. Note that the pupil detector 355 and the corneal reflection detector 356 calculate respective coordinate values of two images obtained by the right and left cameras (step S104).

Note that the right and left cameras are subjected to camera calibration by a stereo calibration method in advance in order to acquire the three-dimensional world coordinates, and a conversion parameter is calculated. As the stereo calibration method, any conventionally used method can be applied, such as a method using the Tsai's camera calibration theory or the like.

The pupil detector 355 and the corneal reflection detector 356 convert the pupil center and the corneal reflection center from the coordinates of the right and left cameras into the three-dimensional world coordinates (step S105). The curvature center calculator 357 obtains a straight line that connects the obtained world coordinates of the corneal reflection center and the obtained world coordinates of the center position of the LED light source 103 (step S106). Next, the curvature center calculator 357 calculates a straight line that connects the world coordinates of the center of the target image displayed at the one point on the screen of the display 101, and the world coordinates of the pupil center (step S107). The curvature center calculator 357 obtains an intersection point of the straight line calculated at step S106 and the straight line calculated at step S107, and employs this intersection point, as the corneal curvature center (step S108). The curvature center calculator 357 calculates the distance between the pupil center and the corneal curvature center of this time, and stores the calculated distance in the storage 150 or the like (step S109). The stored distance is used to calculate the corneal curvature center at the subsequent time of detecting the visual point (visual line).

The distance between the pupil center and the corneal curvature center of when the subject gazes at the one point on the display 101 in the calculation processing is constantly maintained within a range of detecting the visual point in the display 101. The distance between the pupil center and the corneal curvature center may be obtained from an average of entire values calculated during the reproduction of the target image, or may be obtained from an average of values of several times, of values calculated during the reproduction.

Figure 9:
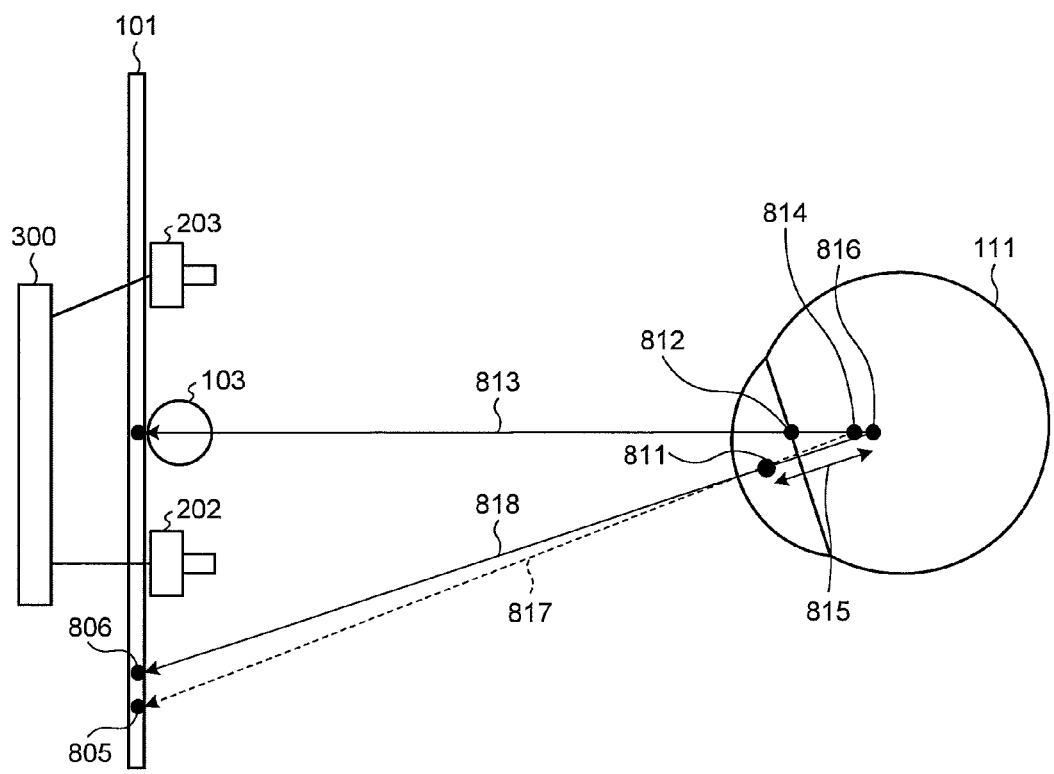
FIG. 9 is a diagram illustrating a method of calculating a corneal curvature center position using a distance obtained in advance.

FIG. 9 is a diagram illustrating a method of calculating a position of a corrected corneal curvature center, using the distance between the pupil center and the corneal curvature center obtained in advance, when the visual point is detected. A gazing visual point 805 indicates the gazing visual point obtained from the corneal curvature center calculated using the typical curvature radius value. A gazing visual point 806 indicates the gazing visual point obtained from the corneal curvature center calculated using the distance obtained in advance.

A pupil center 811 and a corneal reflection center 812 respectively indicate the position of the pupil center calculated at the time of detecting the visual point, and the position of the corneal reflection center. A straight line 813 is a straight line that connects the LED light source 103 and the corneal reflection center 812. A corneal curvature center 814 is the position of the corneal curvature center calculated from the typical curvature radius value. A distance 815 is the distance between the pupil center and the corneal curvature center calculated in the previous calculation processing. A corneal curvature center 816 is the position of the corneal curvature center calculated using the distance obtained in advance. The corneal curvature center 816 is obtained from the facts that the corneal curvature center exists on the straight line 813, and the distance between the pupil center and the corneal curvature center is the distance 815. Accordingly, a visual line 817 calculated when the typical curvature radius value is used is corrected to a visual line 818. Further, the gazing visual point on the screen of the display 101 is corrected from the gazing visual point 805 to the gazing visual point 806.

Figure 10:
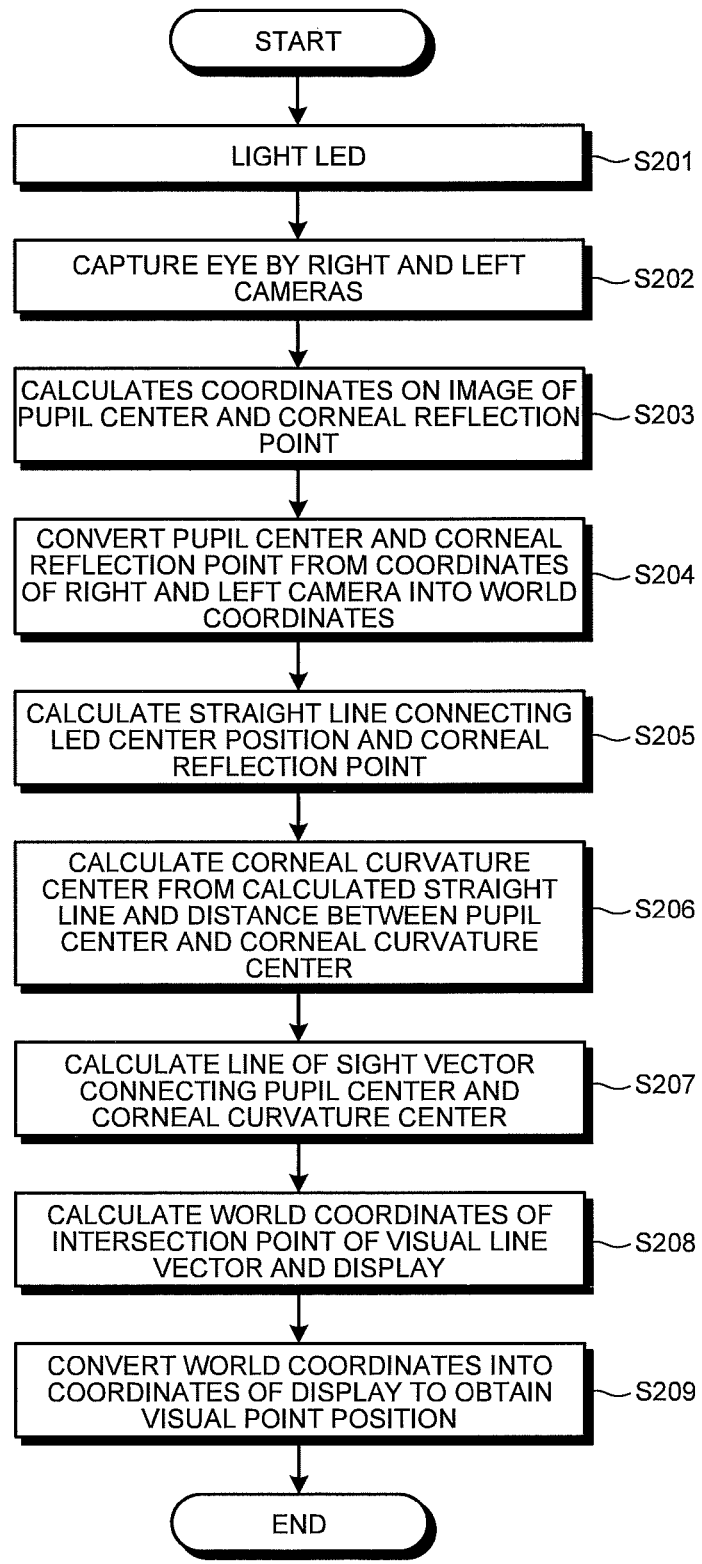
FIG. 10 is a flowchart illustrating an example of visual line detection processing of the present embodiment.

FIG. 10 is a flowchart illustrating an example of visual line detection processing of the present embodiment. For example, as processing of detecting a visual line in diagnosis processing using a diagnosis image, the light of sight detection processing of FIG. 10 can be executed. In the diagnosis processing, processing of displaying a diagnosis image, evaluation processing by the evaluator 361 using the detection result of the gazing visual point, and the like are executed, in addition to the steps of FIG. 10.

Steps S201 to S205 are similar to steps S102 to S106 of FIG. 8, and thus description is omitted.

The curvature center calculator 357 calculates a position where the distance from the pupil center is equal to the distance obtained in the previous calculation processing, on the straight line calculated at step S205, as the corneal curvature center (step S206).

The visual line detector 358 obtains a vector (visual line vector) that connects the pupil center and the corneal curvature center (step S207). This vector indicates the visual line direction that the subject is looking at. The visual point detector 359 calculates three-dimensional world coordinate values of the intersection point of the visual line direction and the screen of the display 101 (step S208). The values are coordinate values that express the one point on the display 101 that the subject gazes at, in the world coordinates. The visual point detector 359 converts the obtained three-dimensional world coordinate values into coordinate values (x, y) expressed in a two-dimensional coordinate system of the display 101 (step S209). Accordingly, the visual point (gazing visual point) on the display 101 that the subject gazes at can be calculated.

First Modification

A pupil detection device (diagnosis supporting device) of a first modification detects a visual line using illuminators installed at two places.

To accurately detect a visual point, it is important to correctly detect a pupil position. It is known that, when a near infrared light source is lighted and the pupil is captured by a camera, the pupil is darker than other parts if the distance between the camera and the light source is separated by a fixed distance or more. By use of this characteristic, the pupil position is detected.

In the above embodiment, one light source is used instead of two light sources, for simplification of the device. With such configuration, there is a case where the pupil does not become sufficiently dark, due to an insufficient distance between the camera and the light source, and the pupil cannot be distinguished from an iris, depending on a subject.

The pupil can be made dark by use of a near infrared light source having a different wavelength and a higher light absorption characteristic. However, it is known that sensitivity of the camera to the wavelength is low and image processing accuracy is deteriorated.

Therefore, in the present modification, light sources are arranged at two places outside respective two cameras. Then, these two light sources are lighted at mutually different timing, and the camera having a longer (farther) distance from the lighted light source captures the subject. Accordingly, the pupil can be captured in a darker manner, and the pupil and other parts can be more accurately distinguished.

In this case, the light sources to be lighted are different, and thus three-dimensional measurement in a regular stereo system cannot be simply applied. That is, a straight line that connects the light source and corneal reflection of when the visual point is obtained cannot be calculated in world coordinates. Therefore, in the present modification, a positional relationship between the cameras to be used for capturing, and a positional relationship between the light sources to be lighted, at two timing, are symmetrical to the position of a virtual light source (virtual light source position). Then, two coordinates obtained at the time of lighting the respective two light sources are converted into the world coordinates, as coordinate values by the left camera and coordinate values by the right camera. Accordingly, the straight line that connects the virtual light source and the corneal reflection point can be calculated in the world coordinates, and the visual point can be calculated based on the straight line, using corneal reflection positions obtained at the time of lighting the respective two light sources.

Figure 11:
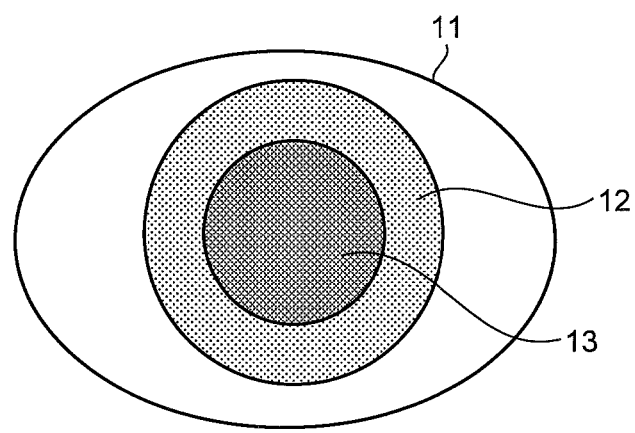
FIG. 11 is a diagram illustrating a state of an eye of a subject of when one light source is used.
Figure 12:
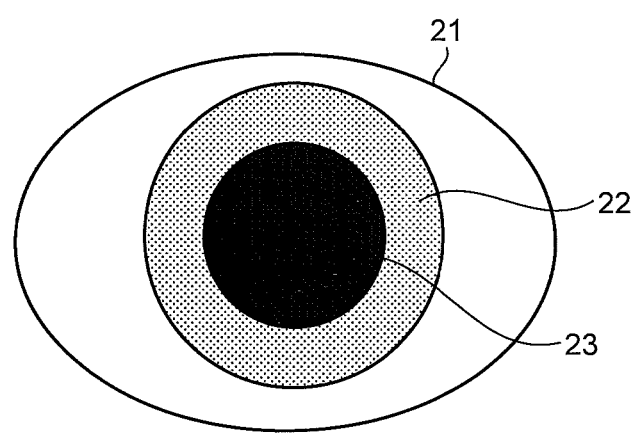
FIG. 12 is a diagram illustrating a state of an eye of a subject of when two light sources are used.

FIG. 11 is a diagram illustrating a state of an eye 11 of a subject of when one light source is used. As illustrated in FIG. 11, a difference of darkness between an iris 12 and a pupil 13 is not sufficient, and discrimination is difficult. FIG. 12 is a diagram illustrating a state of an eye 21 of a subject of when two light sources are used. As illustrated in FIG. 12, the difference of darkness between an iris 22 and a pupil 23 is larger than FIG. 11.

Hereinafter, the present modification will be described using FIGS. 13 to 20. A similar configuration to the above embodiment is denoted with the same reference sign, and description may be omitted.

Figure 13:
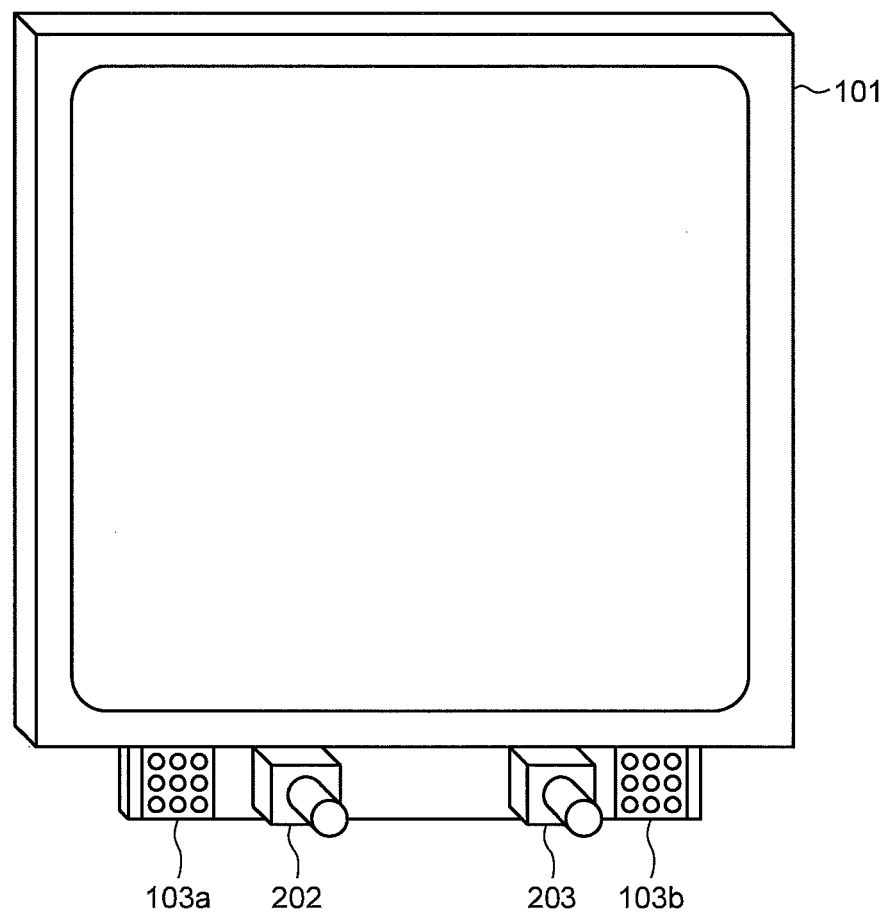
FIG. 13 is a diagram illustrating an example of arrangement of a display, a stereo camera, an infrared light source in a first modification.
Figure 14:
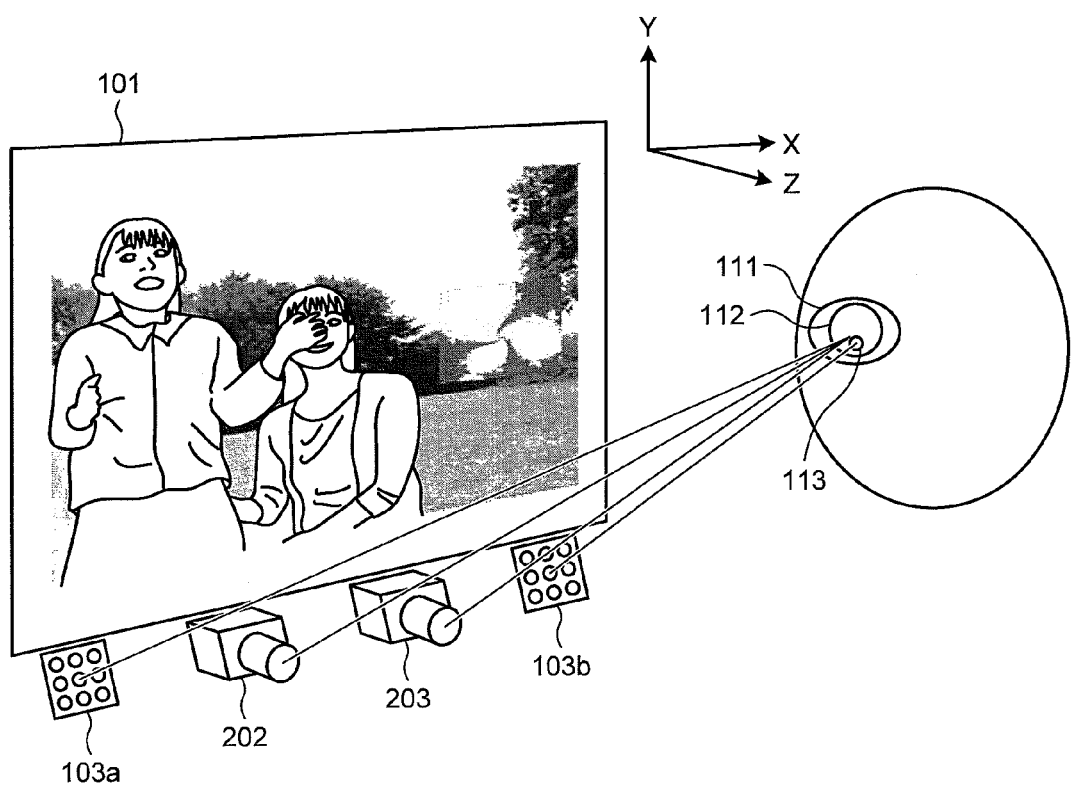
FIG. 14 is a diagram illustrating an example of arrangement of the display, the stereo camera, the infrared light source, and a subject in the first modification.

FIGS. 13 and 14 are diagrams illustrating an example of arrangement of a display, a stereo camera, and infrared light sources of the present modification, and the subject.

As illustrated in FIG. 13, a diagnosis supporting device of the present modification includes a display 101, a right camera 202 and a left camera 203 that configure a stereo camera, and LED light sources 103a and 103b. The right camera 202 and the left camera 203 are arranged under the display 101. The LED light sources 103a and 103b are arranged at outside positions of the right camera 202 and left camera 203, respectively. The LED light sources 103a and 103b are light sources that irradiate the subject with a near infrared ray with a wavelength of 850 nm. FIG. 13 illustrates an example in which nine LEDs configure each of the LED light sources 103a and 103b (illuminator). Note that, for the right camera 202 and the left camera 203, a lens that can transmit the near infrared light with the wavelength of 850 nm is used. Note that the positions of the LED light sources 103a and 103b, and the right camera 202 and the left camera 203 may be reversed, and the LED light sources 103a and 103b may be arranged at inside positions of the right camera 202 and the left camera 203, respectively.

As illustrated in FIG. 14, the LED light sources 103a and 103b irradiate an eye ball 111 of the subject with the near infrared light. The left camera 203 captures the subject when the LED light source 103a irradiates the subject with the light, and the right camera 202 captures the subject when the LED light source 103b irradiates the subject with the light. The positional relationship between the right camera 202 and the left camera 203, and the LED light sources 103a and 103b is appropriately set, so that a pupil 112 is reflected at low luminance and becomes dark, and corneal reflection 113 caused as a virtual image in the eye ball 111 becomes bright, in the captured image. Therefore, the positions of the pupil 112 and the corneal reflection 113 on the image can be obtained by the two cameras (the right camera 202 and the left camera 203).

Figure 15:
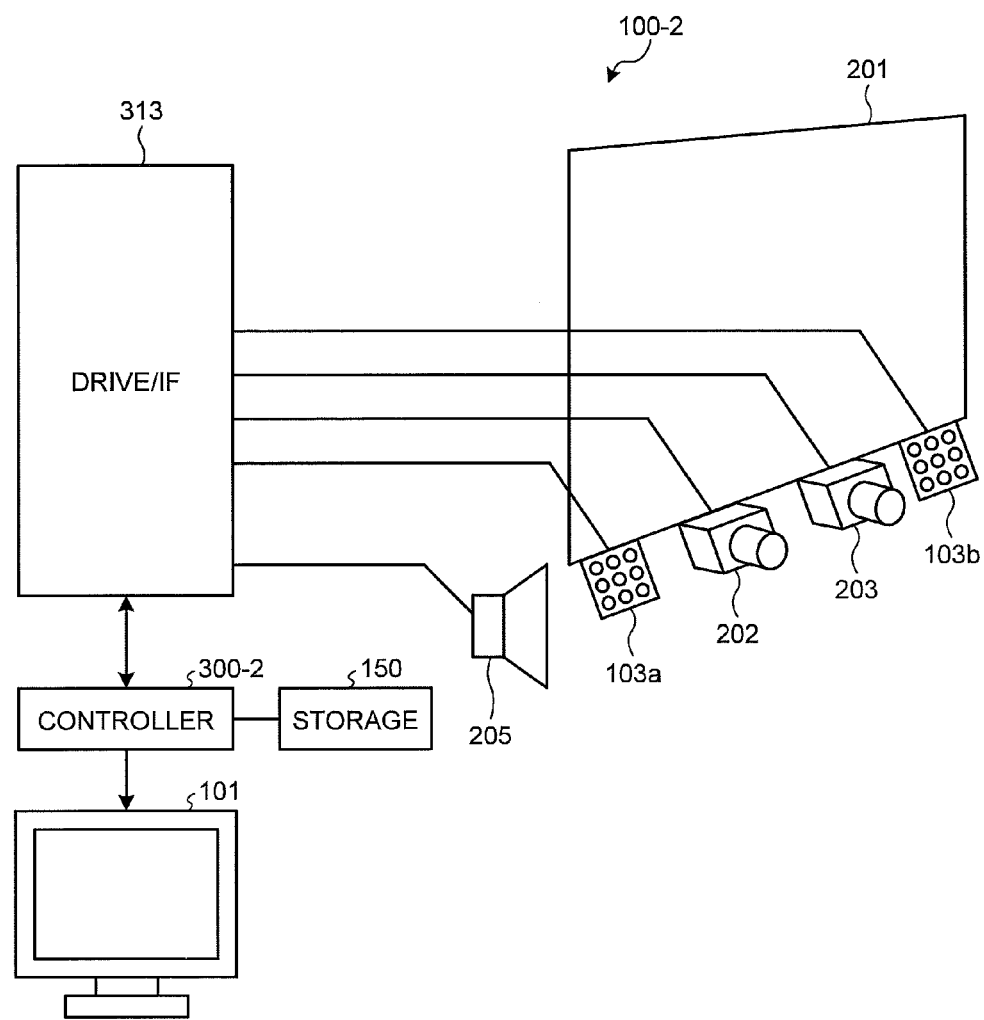
FIG. 15 is a diagram illustrating an outline of functions of a diagnosis supporting device of the first modification.

FIG. 15 is a diagram illustrating an outline of functions of a diagnosis supporting device 100-2. FIG. 15 illustrates a part of the configurations illustrated in FIGS. 13 and 14, and configurations used for driving the aforementioned configurations. As illustrated in FIG. 15, the diagnosis supporting device 100-2 includes the right camera 202 and the left camera 203, the LED light source 103a for the left camera 203 and the LED light source 103b for the right camera 202, a speaker 205, a drive/IF 313, a controller 300-2, a storage 150, and the display 101.

Figure 16:
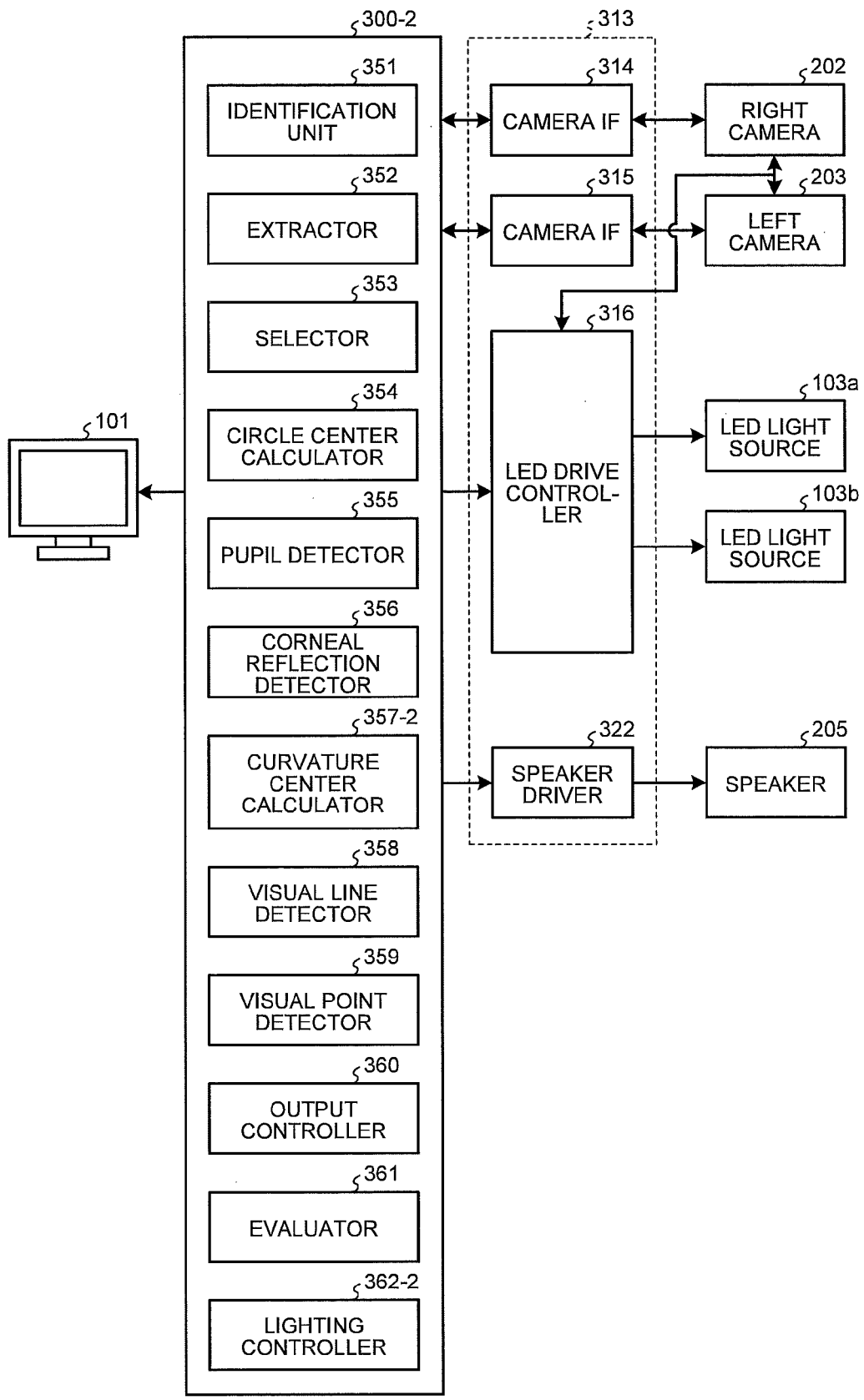
FIG. 16 is a block diagram illustrating an example of detailed functions of respective units illustrated in FIG. 15.

FIG. 16 is a block diagram illustrating an example of detailed functions of respective units illustrated in FIG. 15. As illustrated in FIG. 16, the display 101 and the drive/IF 313 are connected to the controller 300-2.

A frame synchronization signal is output from the right camera 202. The frame synchronization signal is input to the left camera 203 and an LED drive controller 316. Accordingly, the LED light sources 103a and 103b are emitted, and images captured by the right and left cameras 202 are taken in response to the emission.

The controller 300-2 controls the entire diagnosis supporting device 100-2. The controller 300-2 includes an identification unit 351, an extractor 352, a selector 353, a circle center calculator 354, a pupil detector 355, a corneal reflection detector 356, a curvature center calculator 357-2, a visual line detector 358, a visual point detector 359, an output controller 360, an evaluator 361, and a lighting controller 362-2.

The elements (the identification unit 351, the extractor 352, the selector 353, the circle center calculator 354, the pupil detector 355, the corneal reflection detector 356, the curvature center calculator 357-2, the visual line detector 358, the visual point detector 359, the output controller 360, the evaluator 361, and the lighting controller 362-2) included in the controller 300-2 may be realized by software (programs), may be realized by a hardware circuit, or may be realized by use of the software and the hardware circuit together.

In the present modification, addition of the lighting controller 362-2 and the function of the curvature center calculator 357-2 are different from the above embodiment.

The lighting controller 362-2 controls the LED light sources 103a and 103b using the LED drive controller 316. For example, the lighting controller 362-2 controls the LED light sources 103a and 103b to be lighted at mutually different timing. The difference of timing (times) may just be a time that is determined in advance as a time in which no influence is caused to a visual line detection result, due to movement of the visual line of the subject and the like.

The curvature center calculator 357-2 calculates a corneal curvature center (fourth position) from a straight line (first straight line) that connects the virtual light source position and the corneal reflection center. For example, the curvature center calculator 357-2 calculates a position where the distance from the corneal reflection center becomes a predetermined value, on the straight line, as the corneal curvature center. As the predetermined value, a value determined in advance from a curvature radius value of a typical cornea, and the like can be used.

Similarly to the above embodiment, the curvature center calculator 357-2 may calculate the corneal curvature center in consideration of individual difference. In this case, the curvature center calculator 357-2 first calculates an intersection point of a straight line (second straight line) that connects a pupil center and a target position, and the straight line (first straight line that connects the corneal reflection center and the virtual light source position, using the pupil center and the corneal reflection center calculated when the subject is caused to gaze at the target position (third position). Then, the curvature center calculator 357-2 calculates a distance (first distance) between the pupil center and the calculated intersection point, and stores the calculated distance in the storage 150, for example.

Processing up to the calculation of the distance is executed in advance before actual detection of the visual line is started. At the time of actual detection of the visual line, the curvature center calculator 357-2 calculates a position where the distance from the pupil center becomes the distance calculated in advance, on the straight line that connects the virtual light source position and the corneal reflection center, as the corneal curvature center.

Figure 17:
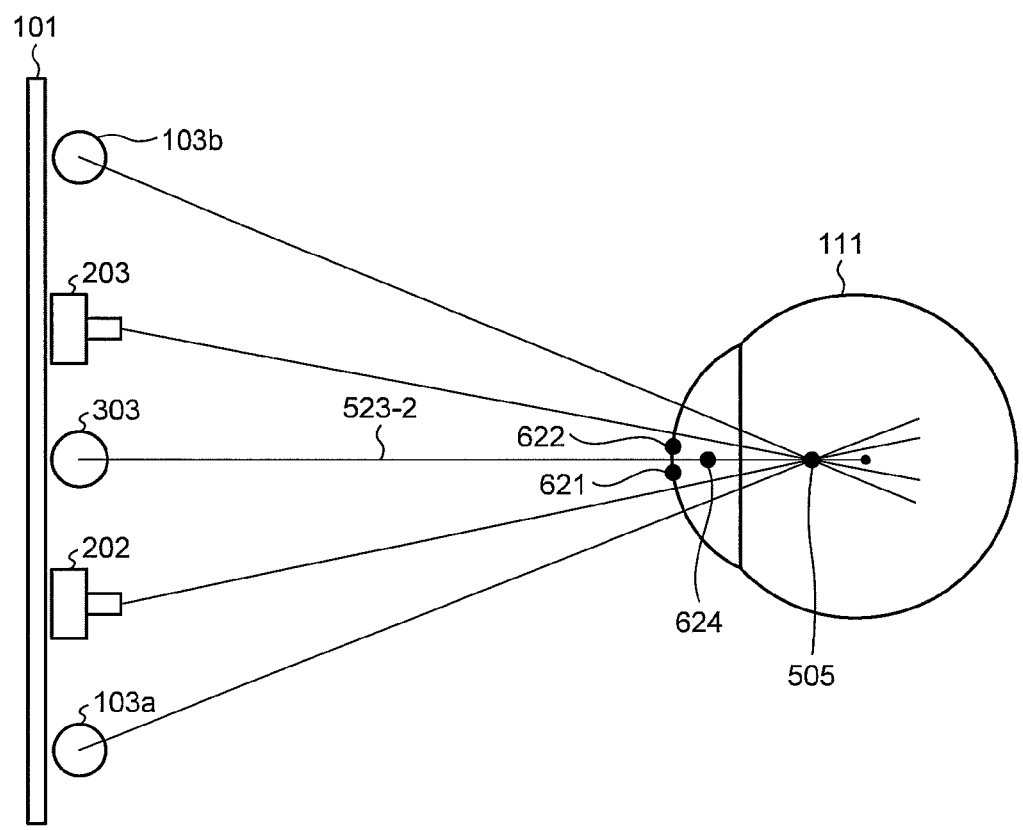
FIG. 17 is a diagram for describing an outline of processing executed by the diagnosis supporting device of the first modification.

FIG. 17 is a diagram for describing an outline of processing executed by the diagnosis supporting device 100-2 of the present modification. Elements described in FIGS. 13 to 16 are denoted with the same reference signs, and description is omitted.

A corneal reflection point 621 indicates a corneal reflection point on an image captured by the left camera 203. A corneal reflection point 622 indicates a corneal reflection point on an image captured by the right camera 202. In the present modification, the right camera 202 and the LED light source 103b for the right camera, and the left camera 203 and the LED light source 103a for the left camera are in a positional relationship symmetrical to a straight line that passes through an intermediate position of the right camera 202 and the left camera 203. Therefore, a virtual light source 303 can be deemed to be positioned at the intermediate position (virtual light source position) of the right camera 202 and the left camera 203. A corneal reflection point 624 indicates a corneal reflection point corresponding to the virtual light source 303. Coordinate values of the corneal reflection point 621 and coordinate values of the corneal reflection point 622 are converted using a conversion parameter for converting coordinate values of right and left cameras into three-dimensional world coordinates, so that world coordinate values of the corneal reflection point 624 can be calculated. A corneal curvature center 505 exists on a straight line 523-2 that connects the virtual light source 303 and the corneal reflection point 624. Therefore, the visual point can be detected by a method equivalent to the visual line detection method in which the light source is in one place illustrated in FIG. 6.

Note that the positional relationship between the right camera 202 and the left camera 203, and the positional relationship between the LED light source 103a and the LED light source 103b are not limited to the above relationships. For example, the respective positional relationships may be symmetrical to the same straight line, or the right camera 202 and the left camera 203, and the LED light source 103a and the LED light source 103b may not be on the same straight line.

Figure 18:
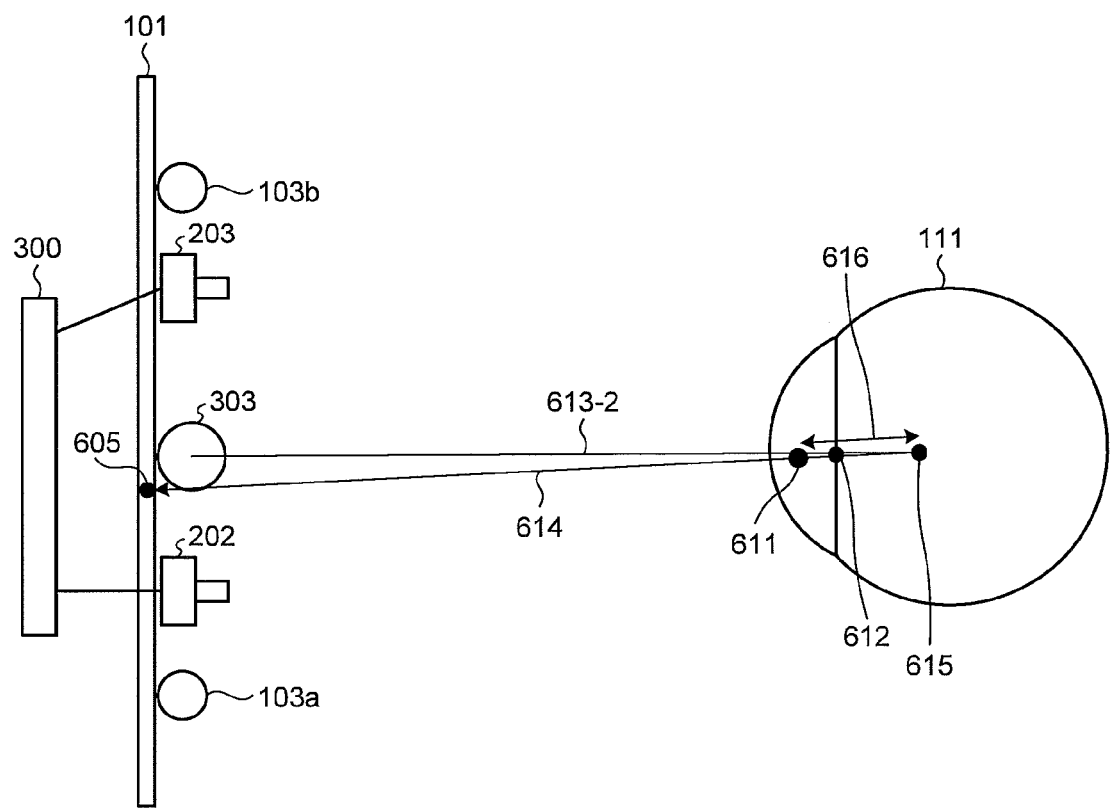
FIG. 18 is a diagram for describing calculation processing of calculating a distance between a pupil center position and a corneal curvature center position.

FIG. 18 is a diagram for describing calculation processing of calculating a corneal curvature center position, and the distance between a pupil center position and the corneal curvature center position, before the visual point (visual line) is detected. Elements described in FIGS. 13 to 16 are denoted with the same reference signs, and description is omitted.

A target position 605 is a position for causing the subject to gaze at, by outputting of a target image or the like to one point on the display 101. In the present modification, the target position 605 is a middle position on the screen of the display 101. A straight line 613-2 is a straight line that connects the virtual light source 303 and a corneal reflection center 612.

Figure 19:
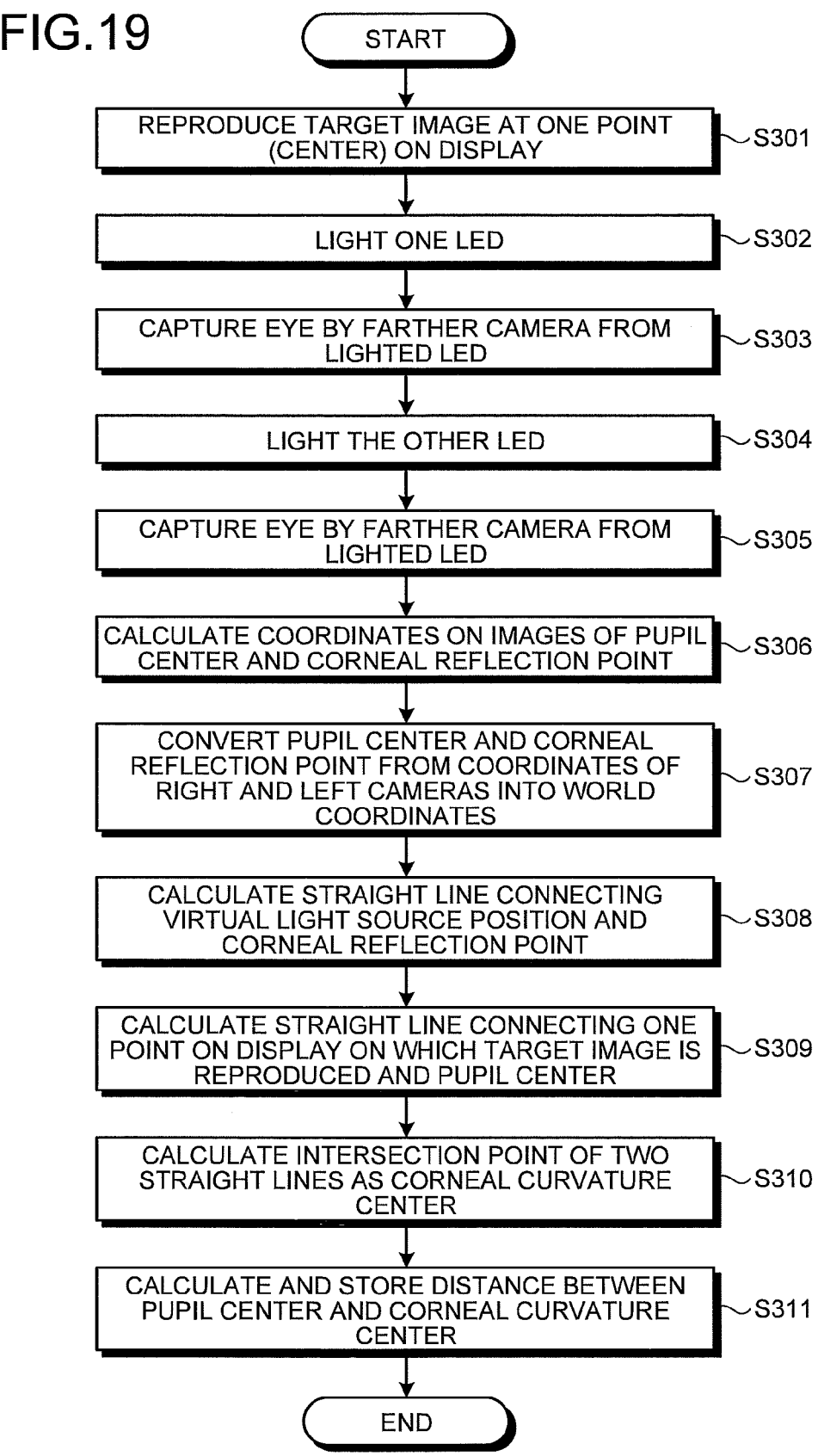
FIG. 19 is a flowchart illustrating an example of the calculation processing of the first modification.

FIG. 19 is a flowchart illustrating an example of calculation processing of the present modification.

First, the output controller 360 reproduces the target image at one point of the screen of the display 101 (step S301), and prompts the subject to gage at the one point. Next, the lighting controller 362-2 lights one of the LED light sources 103a and 103b toward an eye of the subject using the LED drive controller 316 (step S302). The controller 300-2 captures the eye of the subject by the camera having a longer distance from the lighted LED light source, of the right and left cameras (the right camera 202 and the left camera 203) (step S303). Next, the lighting controller 362-2 lights the other of the LED light sources 103a and 103b toward the eye of the subject (step S304). The controller 300-2 captures the eye of the subject by the camera having a longer distance from the lighted LED light source, of the right and left cameras (step S305).

Note that capturing by the camera other than the camera having a longer distance from the lighted LED light source may not be stopped. That is, the eye of the subject is captured at least by the camera having a longer distance from the lighted LED light source, and the captured image can be used for coordinate calculation and the like.

By the irradiation of the LED light source 103a or the LED light source 103b, a pupil part is detected as a dark part (dark pupil). Further, as reflection of the LED irradiation, a virtual image of the corneal reflection occurs, and a corneal reflection point (corneal reflection center) is detected as a bright part. That is, the pupil detector 355 detects the pupil part from the captured image, and calculates coordinates that indicate the position of the pupil center. The pupil detector 355 detects, for example, a region having predetermined brightness or less including the darkest part in a fixed region including the eye, as the pupil part. Further, the corneal reflection detector 356 detects, for example, a region having predetermined brightness or more including the brightest part in a fixed region including the eye, as the corneal reflection. Further, the corneal reflection detector 356 detects a corneal reflection part from the captured image, and calculates coordinates that indicate the position of the corneal reflection center. Note that the pupil detector 355 and the corneal reflection detector 356 calculate coordinate values of respective two images obtained by the right and left cameras (step S306).

The pupil detector 355 and the corneal reflection detector 356 converts the coordinates of the right and left cameras into the three-dimensional world coordinates of the pupil center and the corneal reflection center, using the conversion parameter (step S307). For example, the pupil detector 355 and the corneal reflection detector 356 converts the coordinates of the right camera 202 and the left camera 203 into the three-dimensional world coordinates, using the conversion parameter, where the coordinates obtained from the image captured by the left camera 203 when the LED light source 103a is lighted are the coordinates of the left camera 203, and the coordinates obtained from the image captured by the right camera 202 when the LED light source 103b is lighted are the coordinates of the right camera 202. The world coordinate values obtained as a result of the conversion correspond to world coordinate values obtained from the images captured by the right and left cameras if the virtual light source 303 irradiates the subject with light. The curvature center calculator 357-2 obtains a straight line that connects the obtained world coordinates of the corneal reflection center, and the world coordinates of the center position of the virtual light source 303 (step S308). Next, the curvature center calculator 357-2 calculates a straight line that connects world coordinates of the center of the target image displayed at one point on the screen of the display 101, and the world coordinates of the pupil center (step S309). The curvature center calculator 357-2 obtains an intersection point of the straight line calculated at step S308 and the straight line calculated at step S309, and employs the intersection point as the corneal curvature center (step S310). The curvature center calculator 357-2 calculates the distance between the pupil center and the corneal curvature center of this time, and stores the calculated distance in the storage 150 or the like (step S311). The stored distance is used to calculate the corneal curvature center at the subsequent time of detecting the visual point (visual line).

As a method of calculating the position of the corrected corneal curvature center using the distance between the pupil center and the corneal curvature center obtained in advance, a method similar to that of FIG. 9 described in the above embodiment can be applied.

Figure 20:
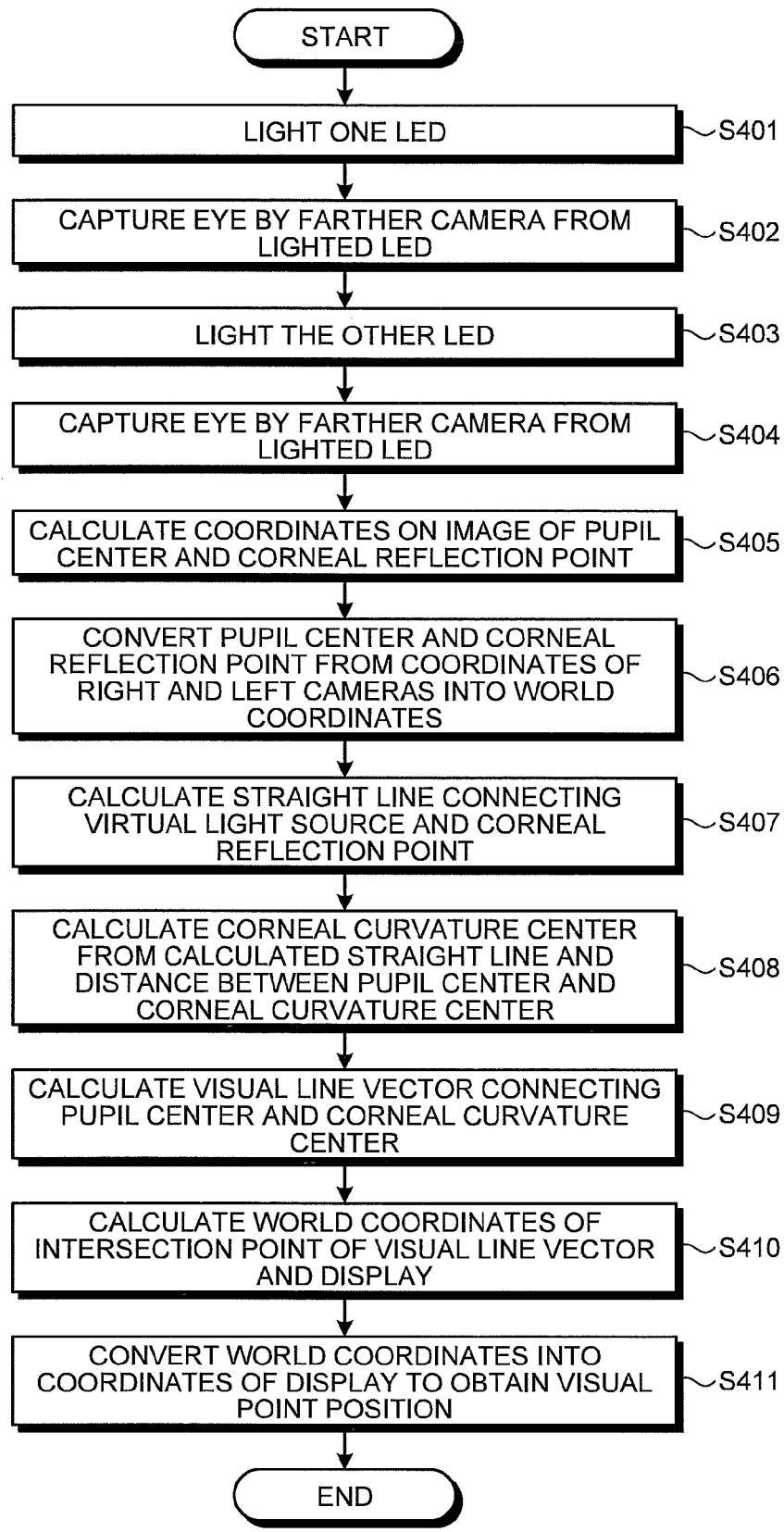
FIG. 20 is a flowchart illustrating an example of visual line detection processing of the first modification.

FIG. 20 is a flowchart illustrating an example of visual line detection processing of the present modification.

Steps S401 to S407 are similar to steps S302 to S308 of FIG. 19, and thus description is omitted. Further, steps S408 to S411 are similar to steps S206 to S209 of FIG. 10, and thus description is omitted.

Second Modification

Processing of calculating a distance between a pupil center position and a corneal curvature center position is not limited to the method described in FIGS. 7 and 8. Hereinafter, another example of the calculation processing will be described using FIGS. 21 and 22.

Figure 21:
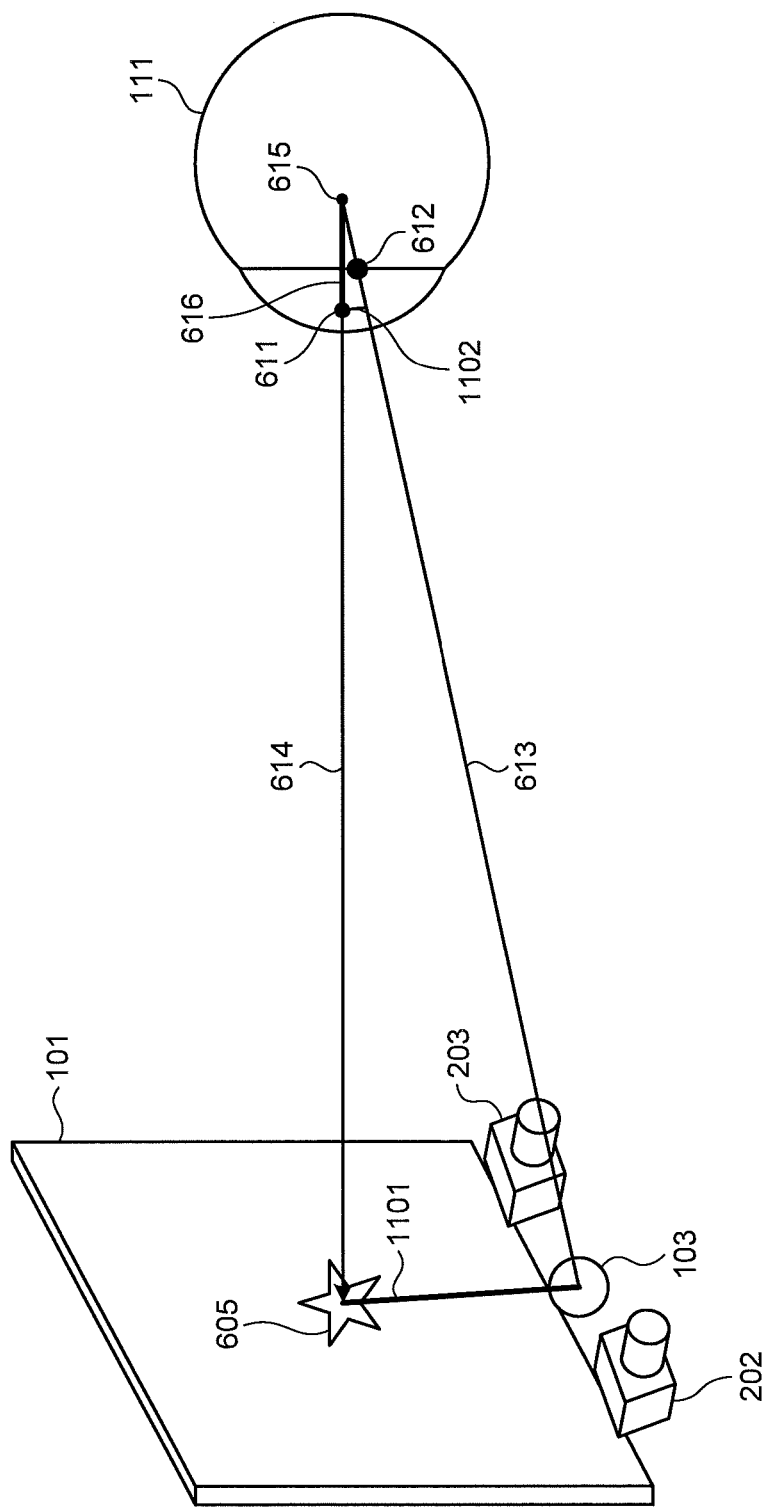
FIG. 21 is a diagram for describing calculation processing of a second modification.

FIG. 21 is a diagram for describing calculation processing of the present modification. Elements described in FIGS. 1 to 4, and 7 are denoted with the same reference signs, and description is omitted.

A line segment 1101 is a line segment (first line segment) that connects a target position 605 and an LED light source 103. A line segment 1102 is a line segment (second line segment) that is parallel to the line segment 1101, and connects a pupil center 611 and a straight line 613. In the present modification, a distance 616 between the pupil center 611 and a corneal curvature center 615 is calculated using the line segment 1101 and the line segment 1102, and stored.

FIG. 22 is a flowchart illustrating an example of calculation processing of the present modification.

Steps S501 to S507 are similar to steps S101 to S107 of FIG. 8, and thus description is omitted.

A curvature center calculator 357 calculates a line segment (the line segment 1101 in FIG. 21) that connects a center of a target image displayed at one point on a screen of a display 101, and a center of the LED light source 103, and calculates the length of the calculated line segment (the length is L1101) (step S508).

The curvature center calculator 357 calculates a line segment (the line segment 1102 in FIG. 21) passing through the pupil center 611, and parallel to the line segment calculated at step S308, and calculates the length of the calculated line segment (the length is L1102) (step S509).

The curvature center calculator 357 calculates a distance 616 between the pupil center 611 and the corneal curvature center 615 based on the fact that a triangle having the corneal curvature center 615, as a vertex, and the line segment calculated at step S508, as a base, and a triangle having the corneal curvature center 615, as a vertex, and the line segment calculated at step S509, as a base have a similarity relationship (step S510). For example, the curvature center calculator 357 calculates the distance 616 such that a ratio of the length of the line segment 1102 to the length of the line segment 1101, and a ratio of the distance 616 to the distance between the target position 605 and the corneal curvature center 615 become equal.

The distance 616 can be calculated by the following formula (A). Note that a distance L614 is the distance from the target position 605 to the pupil center 611.

$$\text{Distance } 616 = (L614 \times L1102)/(L1101 - L1102) \qquad (A)$$

The curvature center calculator 357 stores the calculated distance 616 in the storage 150 and the like (step S511). The stored distance is used to calculate the corneal curvature center at the subsequent time of detecting the visual point (visual line).

Processing of the second modification can be applied to the first modification by replacement of the LED light source 103 with the virtual light source 303.

Hereinafter, a specific example of pupil detection processing will be described using FIGS. 23 to 36.

Figure 23:
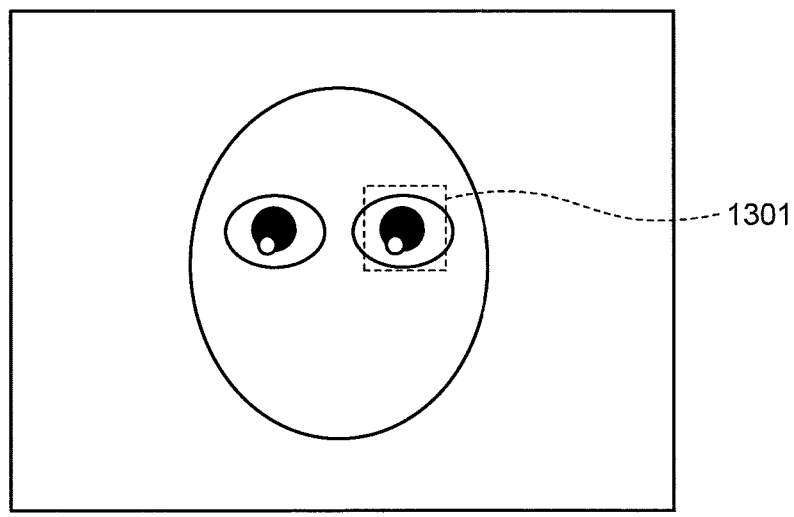
FIG. 23 is a diagram illustrating a captured image captured by a stereo camera.
Figure 24:
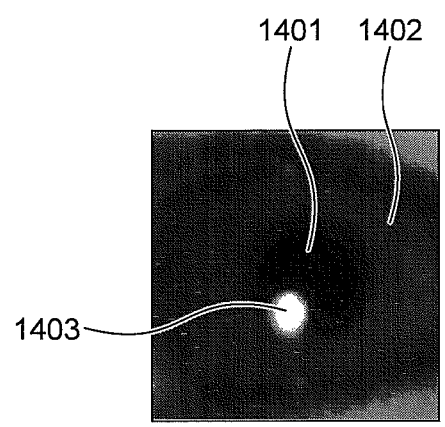
FIG. 24 is a diagram illustrating an example of an eye image cut out of the captured image of FIG. 23.

FIG. 23 is a diagram illustrating an example of a captured image captured by the stereo camera 102. The captured image of FIG. 23 is an example of an image of a captured face of a subject, and includes an eye region 1301. FIG. 24 is a diagram illustrating an example of an eye image of the eye region 1301 cut out of the captured image of FIG. 23. As illustrated in FIG. 24, the eye image includes a pupil 1401, an iris 1402, and a corneal reflection 1403.

Figure 25:
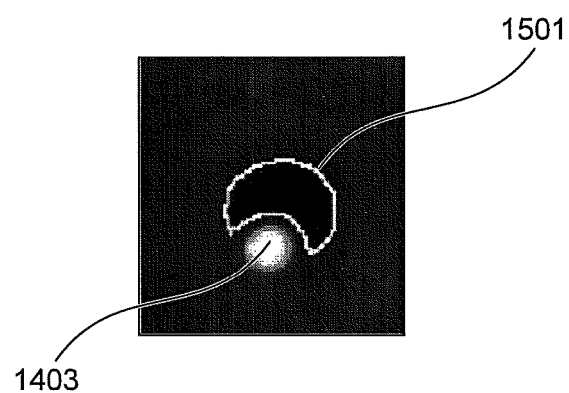
FIG. 25 is a diagram illustrating an example of an extracted contour of a pupil.

Typically, the pupil 1401 is darker than the iris 1402, and is darker than the corneal reflection 1403. FIG. 25 is a diagram illustrating an example of extracted contour (circumference) of the pupil using the luminance differences. Although the contour of the pupil is originally supposed to be a circle, the pupil is often blocked by the corneal reflection 1403, like a contour 1501 of FIG. 25, and a part of the pupil is lacked. Further, the contour 1501 is sometimes lacked due to an influence of hair or an eyelid.

Figure 26:
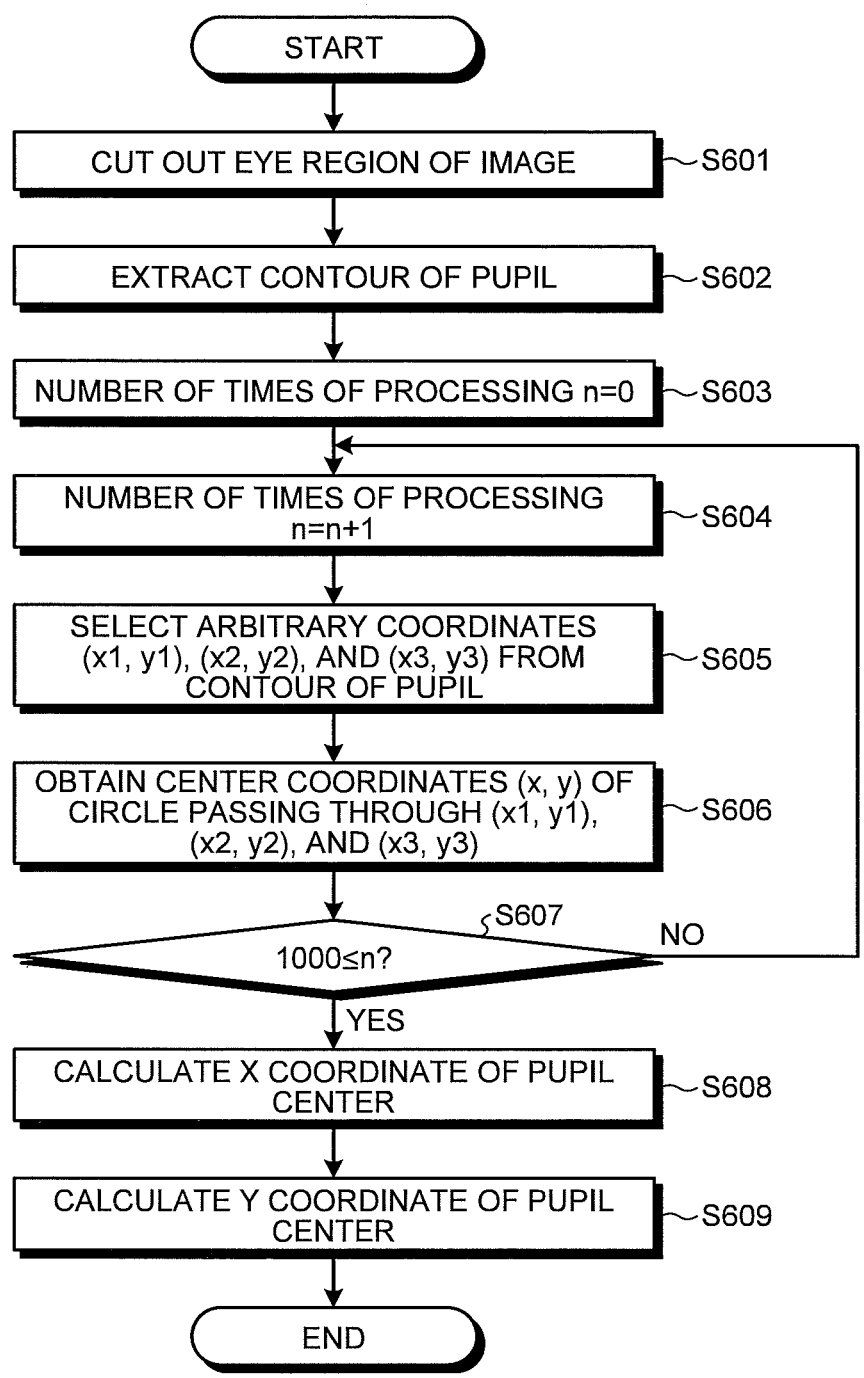
FIG. 26 is a flowchart illustrating an example of pupil detection processing of the present embodiment.

The present embodiment enables obtainment of pupil center as accurate as possible, for the image in which a part of the pupil is lacked. FIG. 26 is a flowchart illustrating an example of pupil detection processing of the present embodiment.

Figure 27:
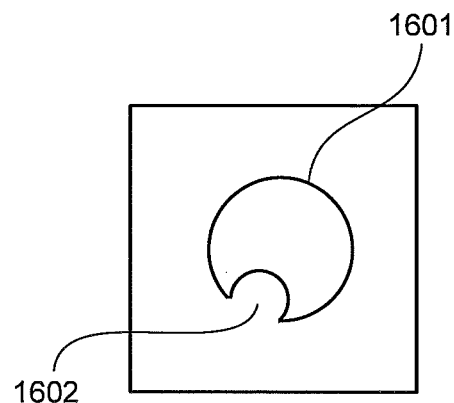
FIG. 27 is a diagram illustrating an example of an extracted contour of the pupil.

An identification unit 351 cut out an eye region of the captured image (step S601). Note that, in a case of a captured image that captures an eye in the entire image, the cut processing may be omitted. The identification unit 351 identifies a pupil region from pixel luminance in the eye region. The identification unit 351 identifies a region having predetermined brightness or less including a darkest region in a fixed region including the eye, as the pupil region. An extractor 352 extracts a contour of the identified pupil region (step S602). FIG. 27 is a diagram illustrating an example of a contour 1601 of the extracted pupil. As illustrated in FIG. 27, the contour 1601 of the pupil is sometimes lacked due to an influence of a corneal reflection region 1602.

Figure 28:
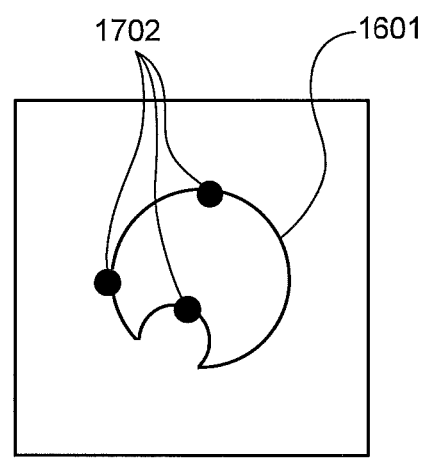
FIG. 28 is a diagram illustrating an example of selected points.

A selector 353 initializes n that is a counter of the number of times of processing to 0 (step S603). The selector 353 adds 1 to the number of times of processing n (step S604). The selector 353 selects a plurality of points on the contour of the pupil (step S605). FIG. 28 is a diagram illustrating an example of selected points 1702. A method of selecting the points may be any method. However, for example, a method of randomly selecting any three points on the contour can be applied.

A circle center calculator 354 calculates the center of the circle passing through the plurality of selected points (step S606). A method of calculating the circle passing through the selected points, and a method of calculating the center of the circle may be any methods. When the method of selecting three points by the selector 353 is applied, the circle center calculator 354 can calculates the center of the circle by the following calculation formula.

Assume that coordinates of the selected three points are (x1, y1), (x2, y2), and (x3, y3). Center coordinates (x, y) of the circle passing through the three points can be obtained by the following formulas (1) to (6):

$$d1 = x1 \times x1 + y1 \times y1 \quad (1)$$

$$d2 = x2 \times x2 + y2 \times y2 \quad (2)$$

$$d3 = x3 \times x3 + y3 \times y3 \quad (3)$$

$$u = 0.5/(x1 \times y2 - x2 \times y1 + x2 \times y3 - x3 \times y2 + x3 \times y1 - x1 \times y3) \quad (4)$$

$$x = u \times (d1 \times y2 - d2 \times y1 + d2 \times y3 - d3 \times y2 + d3 \times y1 - d1 \times y3) \quad (5)$$

$$y = u \times (x1 \times d2 - x2 \times d1 + x2 \times d3 - x3 \times d2 + x3 \times d1 - x1 \times d3) \quad (6)$$

Figure 29:
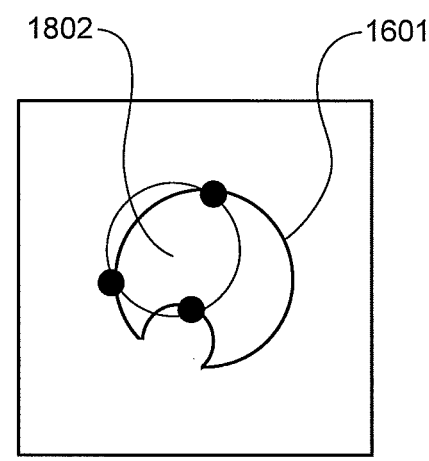
FIG. 29 is a diagram illustrating an example of obtaining center coordinates of a circle that passes through the three points of FIG. 28.

FIG. 29 is a diagram illustrating an example in which center coordinates 1802 of the circle passing through the three points of FIG. 28 are obtained. In this case, one point exists in a lacked part by the corneal reflection and thus the center is shifted from an original pupil center.

Figure 30:
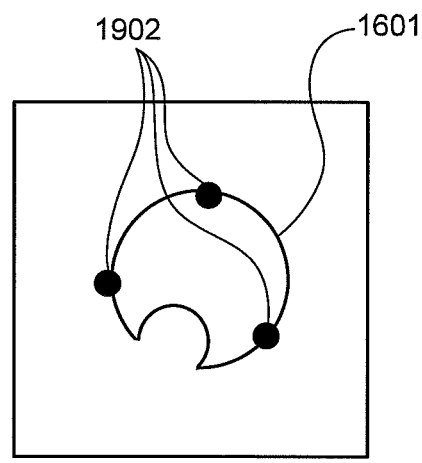
FIG. 30 is a diagram illustrating an example in which three points different from those of FIG. 28 are selected.
Figure 31:
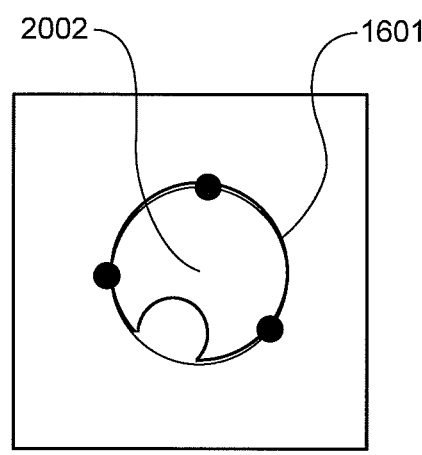
FIG. 31 is a diagram illustrating an example of obtaining center coordinates of a circle that passes through the three points of FIG. 30.

FIG. 30 is a diagram illustrating an example in which three points (points 1902) different from those in FIG. 28 are selected. FIG. 31 is a diagram illustrating an example in which center coordinates 2002 of a circle passing through the three points of FIG. 30 are obtained. In the example of FIG. 30, all of the three points are not caught in the lacked part of the pupil. Therefore, the center coordinates 2002 become a position close to the original pupil center, as illustrated in FIG. 31.

Figure 32:
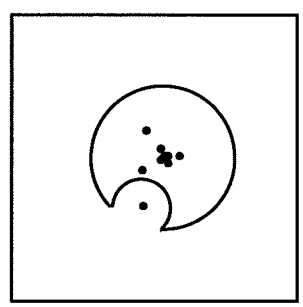
FIG. 32 is a diagram schematically illustrating obtained results of center coordinates of many circles.

FIG. 32 is a diagram schematically illustrating results obtained by selecting random three points on the contour of the pupil, repeatedly performing the processing, and obtaining the center coordinates of many circles. In FIG. 32, each of the black points indicates the obtained center coordinates.

Figure 33:
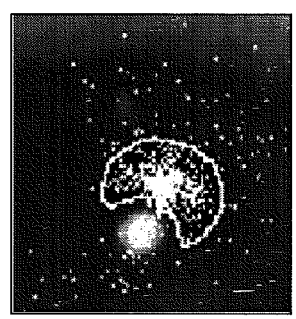
FIG. 33 is a diagram illustrating center coordinates obtained by 1000 times of calculation.
Figure 34:
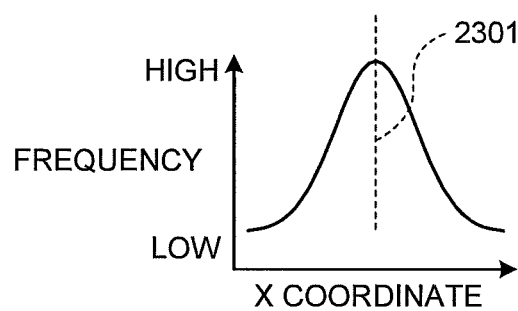
FIG. 34 is a diagram illustrating an example of frequency distribution of the center coordinates in an X direction.
Figure 35:
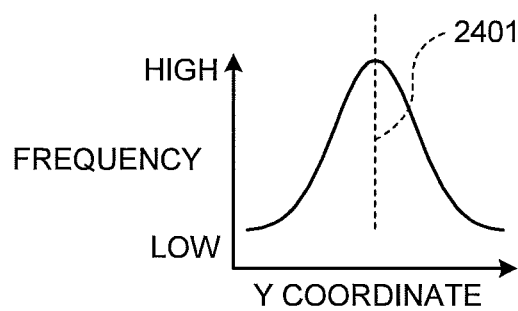
FIG. 35 is a diagram illustrating an example of frequency distribution of the center coordinates in a Y direction.

FIG. 33 is a diagram illustrating an example of the center coordinates obtained by 1000 times of calculation to an actual image. In FIG. 33, each of the white points indicates the obtained center coordinates. FIGS. 34 and 35 are diagrams illustrating examples of frequency distribution of X and Y direction components (X coordinates, Y coordinates) of the center coordinates. The X direction components of the obtained center coordinates show a distribution having an X coordinate 2301 of the original pupil center, as a peak, as illustrated in FIG. 34. Further, similarly, the Y direction components show a distribution having a Y coordinate 2401 of the original pupil center, as a peak, as illustrated in FIG. 35.

As described above, the processing of selecting points by the selector 353, and the calculation processing by the circle center calculator 354 may be executed a plurality of times (N times (N is an integer of 2 or more)). FIG. 26 illustrates an example of a case of N=1000. That is, the selector 353 determines whether the number of times of processing n is 1000 or more (step S607). When the number of times of processing n is less than 1000 (No at step S607), the processing is returned to step S604 and repeated.

When the number of times of processing n is 1000 or more (Yes at step S607), a pupil detector 355 detects the center of the pupil region based on the values of the calculated center coordinates. For example, when N center coordinate values are calculated by N times of the calculation processing, the pupil detector 355 detects the coordinate values of the center of the pupil region by averaging the X coordinates and the Y coordinates of a plurality of center coordinates. The pupil detector 355 calculates the X coordinate value of the pupil region by the following formula (7), for example (step S608). Further, the pupil detector 355 calculates the Y coordinate value of the pupil region by the following formula (8) (step S609). Xi and Yi are the X coordinate values and the Y coordinate values of the center coordinates of the i-th circle (i is an integer that satisfies 1≤i≤N).

$$X \text{ coordinate} = \frac{\sum_{i=1}^{N} Xi}{N} \quad (7)$$

$$Y \text{ coordinate} = \frac{\sum_{i=1}^{N} Yi}{N} \quad (8)$$

The pupil detector 355 may average a plurality of center coordinate values included within a predetermined range from a reference position, of a plurality of center coordinate values. Within the predetermined range from a reference position indicates that differences to respective medians (reference positions) of the X coordinate and the Y coordinate are within the predetermined range. The reference positions are not limited to the medians, and for example, may be coordinate values at which the frequency is maximized.

Figure 36:
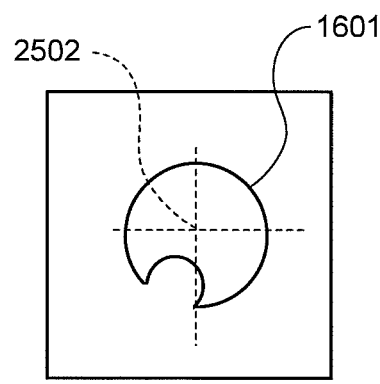
FIG. 36 is a diagram illustrating an example of a pupil center.

FIG. 36 is a diagram illustrating an example of a pupil center 2502 obtained by such processing. As illustrated in FIG. 36, coordinates extremely close to the pupil center can be stably obtained, for the image in which a part of the pupil is lacked.

Figure 37:
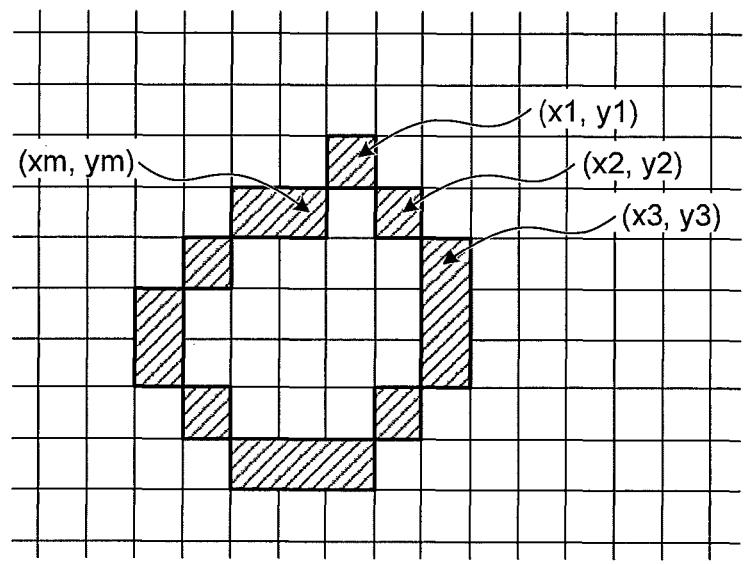
FIG. 37 is a diagram illustrating an example of a contour of a pupil region expressed in pixels.
Figure 38:
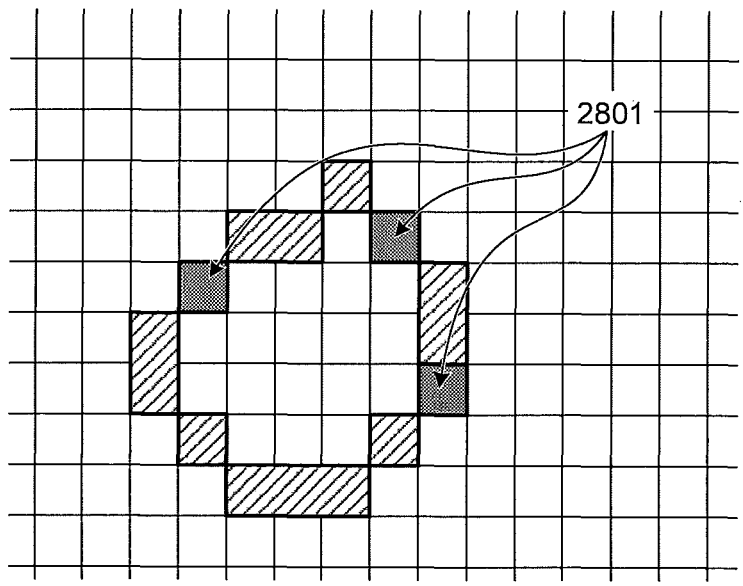
FIG. 38 is a diagram illustrating an example of selected points.

The selection of points by the selector 353 may be realized by the following method. FIG. 37 is a diagram illustrating an example of a contour of a pupil region with points expressed in pixels. As illustrated in FIG. 37, in the image on a computer, coordinates on the contour are expressed in units of pixels (integers). When respective coordinates on the contour are expressed by (x1, y1), (x2, y2), (x3, y3), . . . , and (xm, ym), the selector 353 selects the (pixel) coordinates by selecting three figures by random number from among "1 to m". FIG. 38 is a diagram illustrating an example of selected points 2801.

The selector 353 may perform selection excluding the following cases. That is, when the selected three points satisfy the following conditions, the selector 353 may perform the selection processing again.

(C1) When the selected three points exist on one straight line (this case is excluded because the possibility that the selected three points exist on the same straight line due to an influence of a noise or an error is not zero in an actual image.)

(C2) When a radius value of a circle obtained from the three points is substantially different from those of other circles (this case is excluded because there is a high possibility that the center of the circle is also shifted.)

In the above (C2), the "substantially different" is determined as follows, for example. First, the selector 353 obtains a standard deviation σ of the radius values of all circles. The selector 353 determines that radius values exceeding a range of ±0.5σ from the peak value of a histogram of the radius values, as the substantially different radius values, and excludes the values from objects to be selected. The thresholds ±0.5σ are an example, and the thresholds are not limited thereto. Note that, in this example, the peak value corresponds to the above reference position, and the range of ±0.5σ corresponds to the above predetermined range.

As described above, in the present embodiment, the pupil center can be accurately obtained, for the image in which a part of the pupil is lacked, by the method of repeatedly obtaining coordinates close to the pupil center from different three points on the contour of the pupil, and averaging the coordinates.

Third Modification

In the above method, when the corneal reflection region is caught in the pupil circumference as illustrated in FIG. 27, and the arbitrary point selected randomly exists in the region (for example, FIG. 28), an error of the pupil center becomes large. Therefore, in the present modification, after a contour of a pupil is extracted, processing of deleting a part that might become a cause of the error, of the contour of the pupil, is performed.

Figure 39:
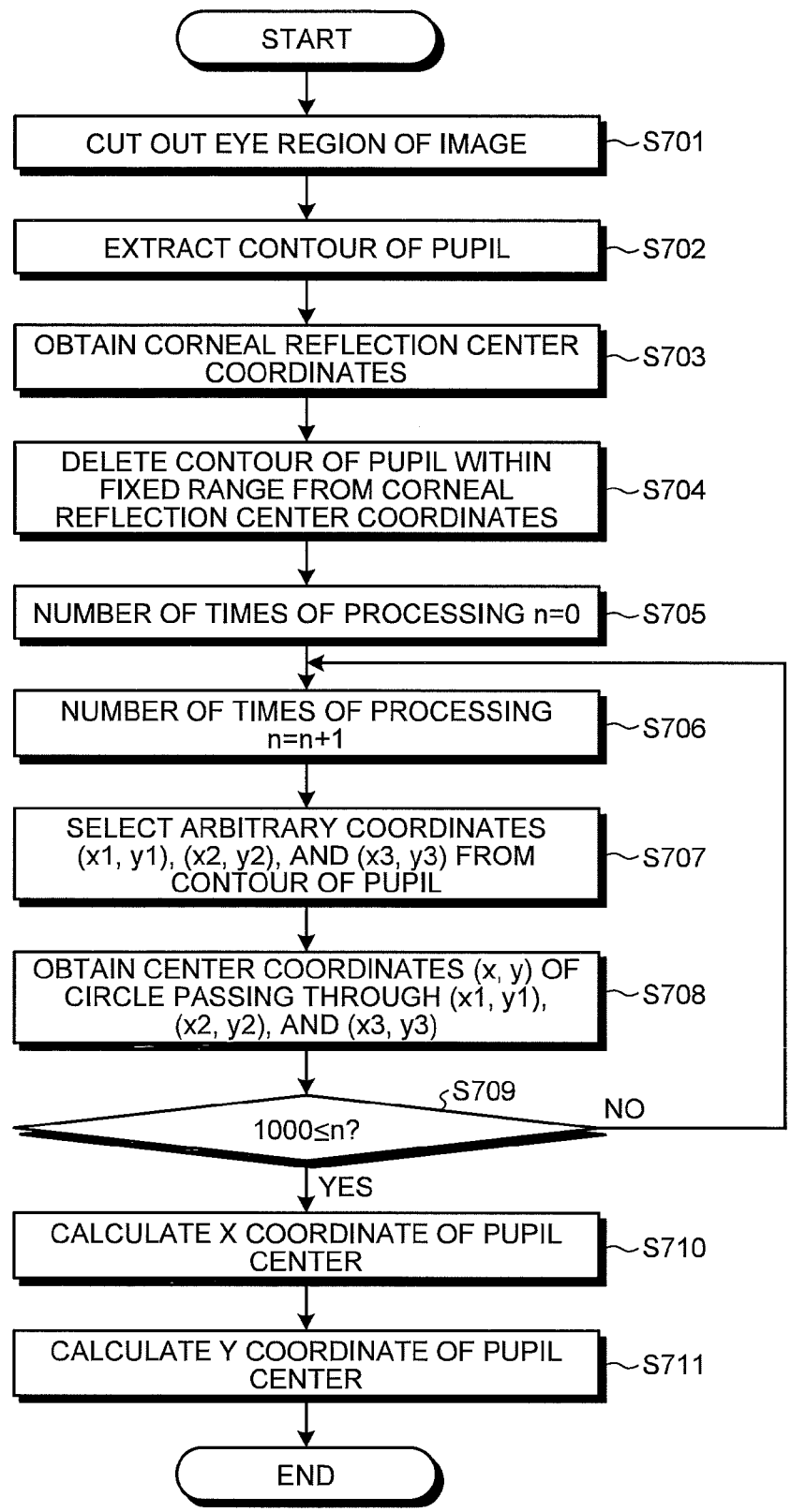
FIG. 39 is a flowchart illustrating an example of pupil detection processing of a third modification.

FIG. 39 is a flowchart illustrating an example of pupil detection processing of the present modification. Steps S701 and S702 are similar to steps S601 and S602 of FIG. 26, and thus description is omitted.

In the present modification, an extractor 352 deletes a predetermined part that might become a cause of an error, from a contour of an extracted pupil. For example, a part in a region within a fixed range from a corneal reflection center, and a part of a contour caused by being hidden by an eyelid due to blink and the like may become causes of an error. In FIG. 39, a case of deleting the part within a fixed range from a corneal reflection center will be exemplarily described.

Figure 40:
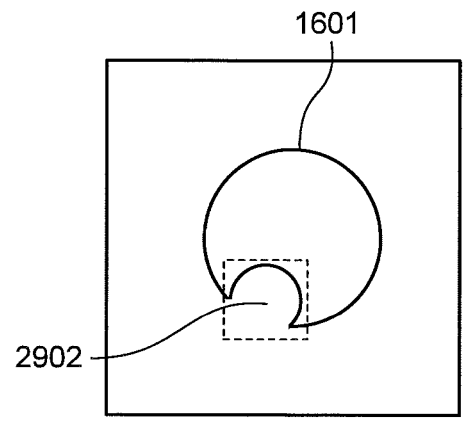
FIG. 40 is a diagram illustrating an example of a detected corneal reflection region.

The extractor 352 obtains corneal reflection center coordinates from a captured image (step S703). For example, the extractor 352 detects a corneal reflection region by a method similar to a corneal reflection detector 356, and obtains the center coordinates of the detected corneal reflection region. FIG. 40 is a diagram illustrating an example of a detected corneal reflection region 2902.

The corneal reflection detector 356 may execute the processing of this step instead of the extractor 352. Further, the extractor 352 may obtain the corneal reflection region and the center coordinates of the corneal reflection region by a different method from that of the corneal reflection detector 356.

Figure 41:
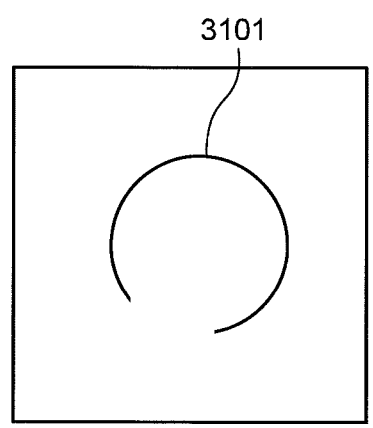
FIG. 41 is a diagram illustrating an example of a contour of a pupil.

The extractor 352 deletes a contour of the pupil within a fixed range from the corneal reflection center coordinates, from the contour of the pupil extracted at step S703 (step S704). FIG. 41 is a diagram illustrating an example of a contour 3101 of the pupil after the deletion.

Subsequent steps S705 to S711 are similar to steps S603 to S609 of FIG. 26, and thus description is omitted.

For example, at step S709, processing of selecting points by a selector 353, and calculation processing by a circle center calculator 354 are executed a plurality of times (N times (N is an integer of 2 or more)) (FIG. 39 illustrates an example of N=1000), an image of a contour of an actual pupil has unevenness, and the actual pupil does not have a perfect circumference. Therefore, the processing is executed the plurality of times.

Figure 42:
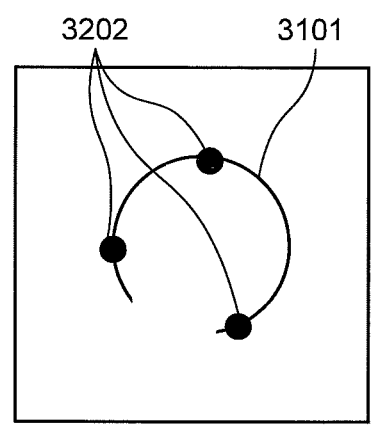
FIG. 42 is a diagram illustrating an example of points selected from a contour of a pupil.

For example, at step S707, arbitrary three points are randomly selected from the contour of the pupil after the deletion. FIG. 42 is a diagram illustrating an example of points 3202 selected from the contour 3101 of the pupil after the deletion.

Figure 43:
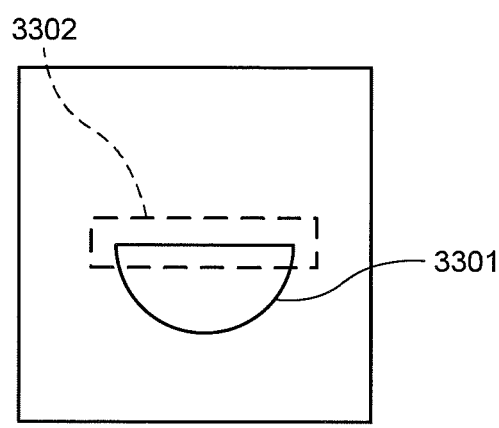
FIG. 43 is a diagram for describing an example in which a part of a pupil is hidden.

FIG. 43 is a diagram for describing an example in which a part of the pupil is hidden by an eyelid. A contour 3301 of the pupil indicates a contour of the pupil extracted in this example. A region 3302 indicates a region including the part of the contour caused by being hidden by the eyelid. The extractor 352 may detect such a region and delete a contour in the region. For example, the region 3302 can be detected as a region including a linear part (a straight line part) that does not configure the circumference, of the contour of the extracted pupil. The linear part may be detected and the detected linear part may be deleted from the contour of the pupil without detecting the region 3302. Note that a method of detecting the predetermined part that might become a cause of an error, of the contour of the pupil, is not limited to the above method.

Figure 44:
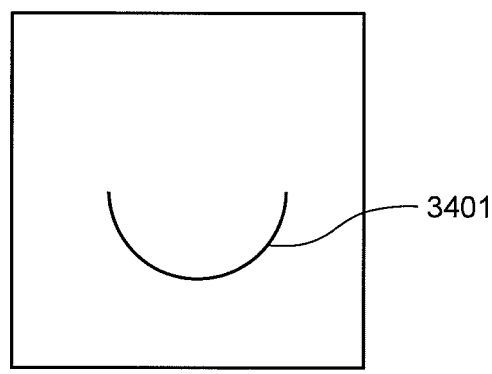
FIG. 44 is a diagram illustrating an example of a contour of a pupil.

FIG. 44 is a diagram illustrating an example of a contour 3401 of the pupil after a part included in the region 3302 is deleted from the contour 3301 of the pupil of FIG. 43. By deletion of a predetermined part that might become a cause of an error, the detection accuracy can be further improved.

As described above, according to the present embodiment, the following advantageous effects can be obtained, for example.
(1) The pupil center coordinates can be stably obtained from the image in which a part of the pupil is lacked by the corneal reflection or the eyelid.
(2) The visual line can be detected with a light source (illuminator) at one place.
(3) The light source is arranged at one place, whereby the device can be made compact, and reduction of cost can be realized.
(4) When the light sources (two light sources) at two places are used, an image of when the light source farther from the two cameras, of the two light sources, is lighted is captured and used, whereby only the pupil can be captured in a darker manner, and the pupil detection accuracy and the visual line detection accuracy can be improved.
(5) One light source farther from the cameras, of the two light sources, is used. Therefore, it is not necessary to separate the two light sources, compared with conventional methods, and the device can be made compact.

The pupil detection device and the pupil detection method according to the present invention exert an advantageous effect to detect a pupil in a high accurate manner, even for an image or the like in which a part of the pupil is lacked.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A pupil detection device comprising:
    an identification unit that is configured to calculate and to identify a pupil region and a corneal reflection region from a captured image of an eye;
    an extractor that is configured to extract a contour of the pupil region identified by the identification unit;
    a selector that is configured to select a plurality of points on the contour of the pupil region extracted by the extractor;
    a center calculator is configured to calculate a center of a circle passing through the plurality of points selected by the selector; and
    a pupil detector that is configured to detect a center of the pupil region from the center of a circle calculated by the center calculator, wherein
    the extractor is further configured to delete a predetermined part of the corneal reflection region from the contour of the pupil region extracted, and the selector is further configured to select the plurality of points on the contour of the pupil region from which the predetermined part of the corneal reflection region has been deleted.

2. The pupil detection device according to claim 1, wherein
the selector is further configured to randomly select the plurality of points on the contour of the pupil region extracted by the extractor.

3. The pupil detection device according to claim 1, wherein
the selector is further configured to execute selection processing of selecting the plurality of points N times (N is an integer of 2 or more), and
the center calculator is further configured to execute calculation processing of calculating the center of a circle passing through the plurality of points selected by the selection processing N times.

4. The pupil detection device according to claim 3, wherein
the pupil detector is further configured to detect the center of the pupil region by averaging a plurality of the centers of circles calculated by the N times of the calculation processing.

5. The pupil detection device according to claim 4, wherein
the pupil detector is further configured to detect the center of the pupil region by averaging a plurality of the centers of circles included in a predetermined range, of the N centers of circles calculated by the N times of the calculation processing.

6. A pupil detection method comprising:
calculating and identifying a pupil region and a corneal reflection region from a captured image of an eye;
extracting a contour of the pupil region identified in the identification step;
selecting a plurality of points on the contour of the pupil region extracted in the extraction step;
calculating a center of a circle passing through the plurality of points selected in the selection step; and
detecting a center of the pupil region from the center of a circle calculated in the center calculation step, wherein
in the extraction step a predetermined part of the corneal reflection region is deleted from the contour of the pupil region extracted, and
in the selection step the plurality of points on the contour of the pupil region from which the predetermined part of the corneal reflection region has been deleted is selected.

* * * * *